(12) United States Patent
Du et al.

(10) Patent No.: US 9,371,429 B2
(45) Date of Patent: *Jun. 21, 2016

(54) LADDER POLYMERS WITH INTRINSIC MICROPOROSITY AND PROCESS FOR PRODUCTION THEREOF

(71) Applicants: Naiying Du, Ottawa (CA); Michael D. Guiver, Ottawa (CA); Gilles P. Robertson, Gatineau (CA)

(72) Inventors: Naiying Du, Ottawa (CA); Michael D. Guiver, Ottawa (CA); Gilles P. Robertson, Gatineau (CA)

(73) Assignee: National Research Council of Canada, Ottawa, Ontario ( * ) Notice: Subject to any disclaimer, the term of this patent is extended or adjusted under 35 U.S.C. 154(b) by 0 days.

This patent is subject to a terminal disclaimer.

(21) Appl. No.: 14/206,065

(22) Filed: Mar. 12, 2014

(65) Prior Publication Data
US 2014/0243441 A1   Aug. 28, 2014

Related U.S. Application Data

(63) Continuation of application No. 13/063,816, filed as application No. PCT/CA2009/001472 on Oct. 16, 2009, now Pat. No. 8,686,104.

(60) Provisional application No. 61/193,081, filed on Oct. 27, 2008.

(51) Int. Cl.
| C08G 59/06 | (2006.01) |
| C08G 59/14 | (2006.01) |
| C08G 65/40 | (2006.01) |
| C08J 9/00 | (2006.01) |
| B01D 53/02 | (2006.01) |
| B01D 53/22 | (2006.01) |
| B01D 71/76 | (2006.01) |
| B01J 20/26 | (2006.01) |
| B01J 20/28 | (2006.01) |
| C07D 339/08 | (2006.01) |
| C08G 75/23 | (2006.01) |
| C08G 59/00 | (2006.01) |
| C08G 65/00 | (2006.01) |

(52) U.S. Cl.
CPC . *C08J 9/00* (2013.01); *B01D 53/02* (2013.01); *B01D 53/228* (2013.01); *B01D 71/76* (2013.01); *B01J 20/26* (2013.01); *B01J 20/262* (2013.01); *B01J 20/2808* (2013.01); *B01J 20/28033* (2013.01); *C07D 339/08* (2013.01); *C08G 65/40* (2013.01); *C08G 65/4006* (2013.01); *C08G 75/23* (2013.01); *B01D 2253/202* (2013.01); *B01D 2256/12* (2013.01); *B01D 2256/22* (2013.01); *B01D 2257/102* (2013.01); *C08L 2205/05* (2013.01);
(Continued)

(58) Field of Classification Search
CPC .................................................. C08G 59/06
USPC ............. 528/106, 86, 88, 104, 109, 403, 425, 528/488, 492
See application file for complete search history.

(56) References Cited

U.S. PATENT DOCUMENTS 8,686,104 B2 * 4/2014 Du et al. ...................... 528/106

OTHER PUBLICATIONS

Du et al (2008), Macromolecules, 41, 9656-9662.*
Budd et al, (2004), Chem Commun. 230-0231.*

* cited by examiner 5,5',6,6'-tetrahydroxy-3,3,3',3'-tetramethylspirobisindane (TTSBI)

2,2'3,3'-tetrahydroxy-1,1'-dinaphthyl (THDN)

2,3,5,6-tetrafluoroterephthalonitrile (TFTPN)

heptafluoro-p-tolylphenylsulfone (HFTPS)

1,2,4,5-tetrafluoro-3,6-bisphenylsulfonylbenzene (TFBPSB)

1,2,4,5-tetrafluoro-3,6-bis(methoxy-4-phenylsulfonyl) benzene (TFBMPSB)

1,2,4,5-tetrafluoro-3,6-bis(ethylsulfonyl) benzene (TFBESB)

2,3,7,8-tetrafluoro-5,5',10,10'-tetraoxidethianthrene (TFTOT)

Primary Examiner — Duc Truong
(74) Attorney, Agent, or Firm — Catherine Lemay

(57) ABSTRACT

A polymer of formula (I):

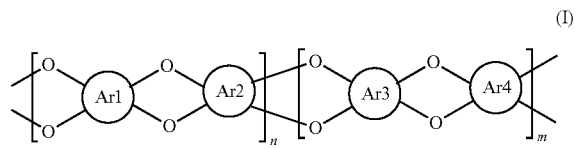

where: n is an integer from 10 to 5,000; m is an integer from 10 to 5,000; Ar1 and Ar3 are the same or different and are residues derived from a tetra-hydroxy aromatic monomer, the tetra-hydroxy aromatic monomer being

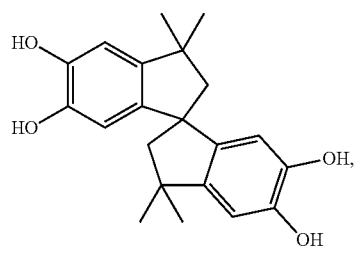

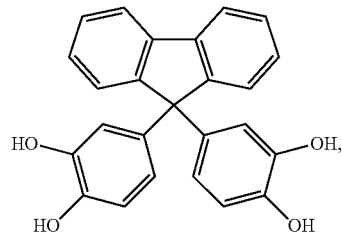

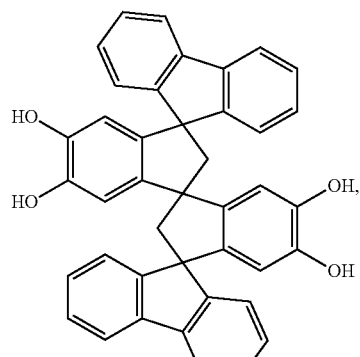

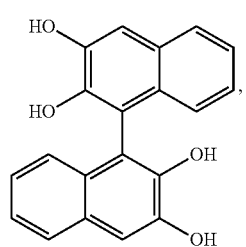

-continued

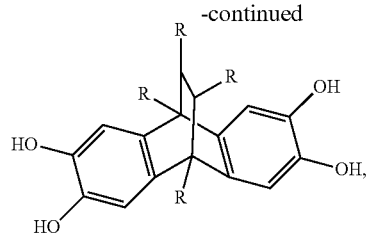

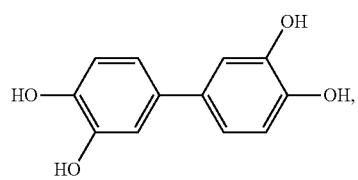

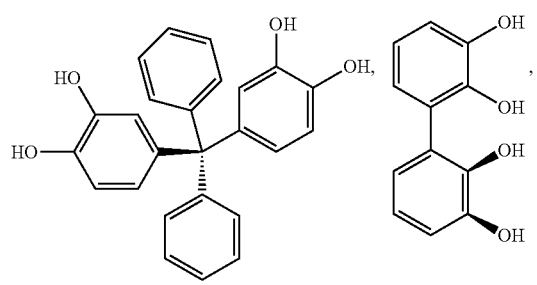

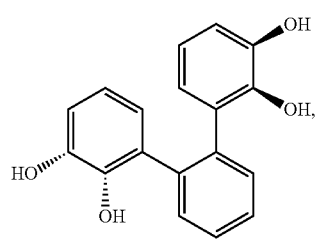

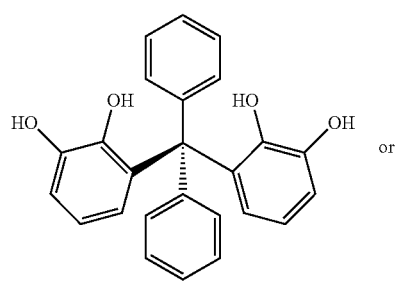

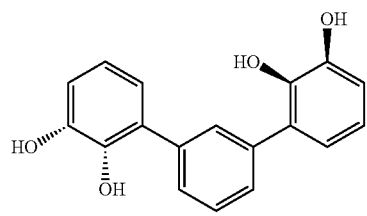

wherein R is the same or different and is H or a $C_1$-$C_8$ alkyl, $C_2$-$C_8$ alkenyl or $C_3$-$C_8$ cycloalkyl group; and, Ar2 and Ar4 are the same or different and are residues derived from a tetra-halogenated aromatic monomer, the tetra-halogenated aromatic monomer being

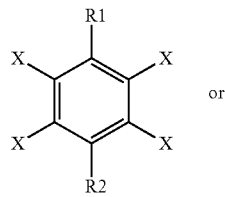
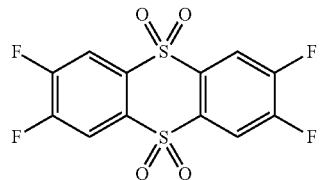
wherein X is F, Cl or Br, and R1 and R2 are the same or different and are
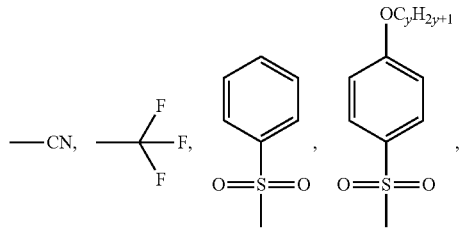
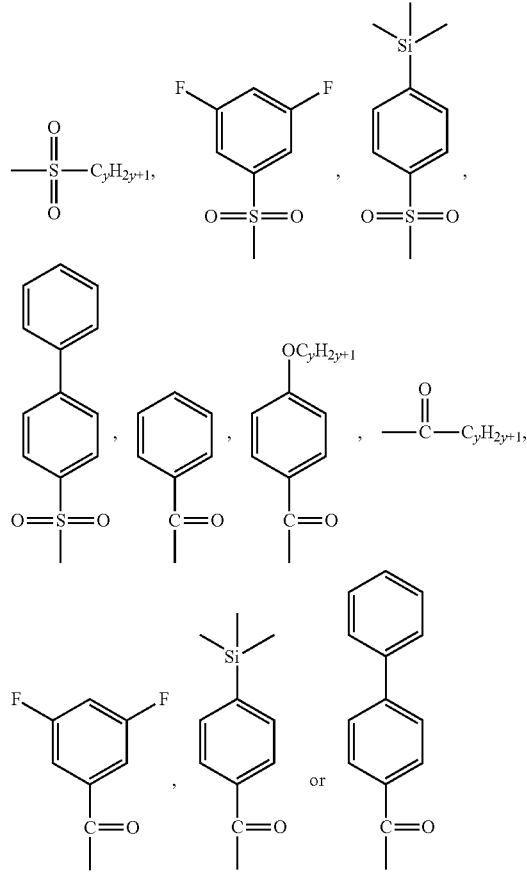
wherein y is an integer from 1 to 8; with the proviso that when Ar1 is the same as Ar3 and Ar2 is the same as Ar4, R1 and R2 are not both —CN is useful as a material for gas separation, vapor separation, adsorbents or catalysis.
18 Claims, 12 Drawing Sheets

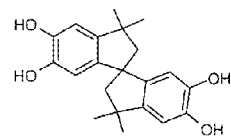

5,5',6,6'-tetrahydroxy-3,3,3',3'-tetramethylspirobisindane
(TTSBI)

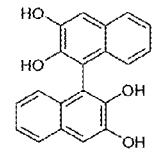

2,2'3,3'-tetrahydroxy-1,1'-dinaphthyl
(THDN)

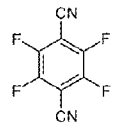

2,3,5,6-tetrafluoroterephthalonitrile
(TFTPN)

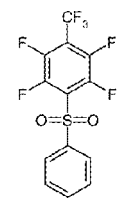

heptafluoro-p-tolylphenylsulfone
(HFTPS)

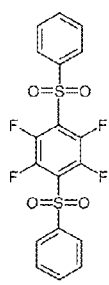

1,2,4,5-tetrafluoro-3,6-bisphenylsulfonylbenzene
(TFBPSB)

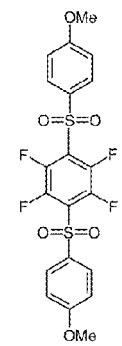

1,2,4,5-tetrafluoro-3,6-bis(methoxy-4-phenylsulfonyl) benzene
(TFBMPSB)

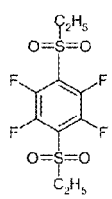

1,2,4,5-tetrafluoro-3,6-bis(ethylsulfonyl) benzene
(TFBESB)

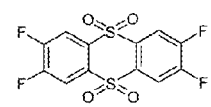

2,3,7,8-tetrafluoro-5,5',10,10'-tetraoxidethianthrene
(TFTOT)

Fig. 1A

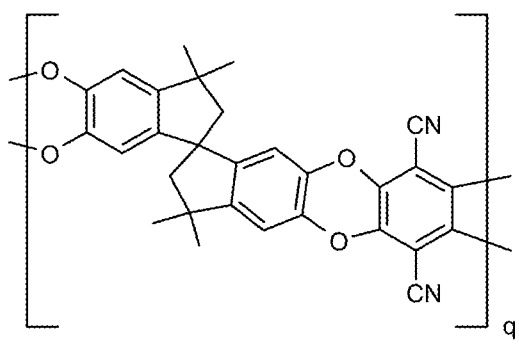
PIM-1
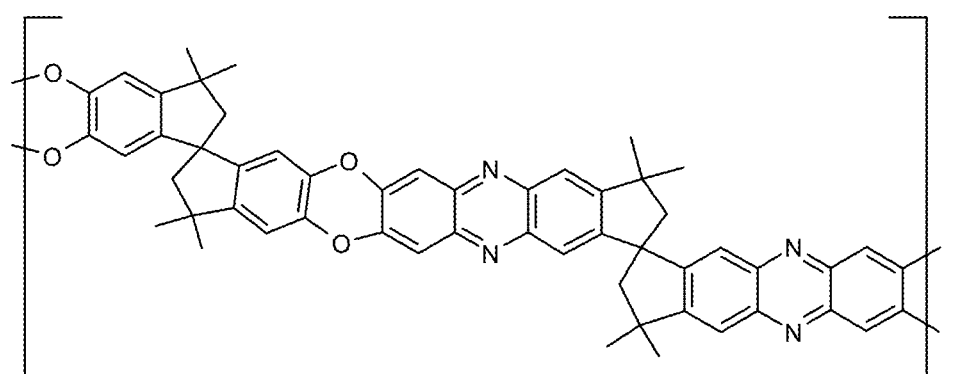
PIM-7
Fig. 1B – Prior Art

I the first substitution reaction
II the second substitution reaction

LADDER POLYMERS WITH INTRINSIC MICROPOROSITY AND PROCESS FOR PRODUCTION THEREOF

CROSS-REFERENCE TO RELATED APPLICATIONS

This application is a continuation of U.S. patent application Ser. No. 13/063,816 filed Mar. 14, 2011 now U.S. Pat. No. 8,686,104, currently pending, which is a national stage filing under 35 U.S.C. §371 of international application PCT/CA2009/001472 filed Oct. 16, 2009, which claims the benefit of U.S. Provisional Patent Application U.S. Ser. No. 61/193,081 filed Oct. 27, 2008, the entire contents of both of which are herein incorporated by reference.

FIELD OF THE INVENTION

The present invention relates to organic polymers, particularly to ladder polymers as materials for membrane gas separation and to processes for producing such ladder polymers.

BACKGROUND OF THE INVENTION

Polymeric microporous materials have had a great impact on academic research and industrial applications. To date, several types of microporous polymeric materials have been reported, for example solvent swollen crosslinked polymers (e.g., hypercrosslinked polystyrenes) [Davankov 1990; Tsyurupa 2002], rigid polymer networks [Budd 2003; McKeown 2006b; Webster 1992; Urban 1995; Wood 2007; McKeown 2002], rigid non-network polymers such as poly(1-trimethylsilyl-1-propyne) [Masuda 1983; Nagai 2001], certain polyimides [Tanaka 1992; Weber 2007], and a number of fluorinated polymers [Yu 2002] or polymers with bulky structural units [Dai 2004; Dai 2005]. Such microporous materials are of potential use in applications such as adsorbents, separation materials, and catalysis, since they combine high internal surface area (comparable with conventional microporous materials, such as zeolites or activated carbons) with the processability of polymers.

Polymer membrane gas separation is a dynamic and rapidly growing field of separation technology [Stem 1994; Maier 1998] because it can offer a number of advantages, such as low energy use and capital cost [Pandey 2001]. In recent years, much effort has been devoted to the design and preparation of membrane materials whose transport properties are improved by overcoming the "trade-off" behavior between permeability and selectivity [Kim 1988; Lee 1988; Robeson 1991; Robeson 1994].

Recently, Budd and co-workers described a novel class of high-free volume polymeric microporous materials derived from nitrile monomers termed "polymers of intrinsic microporosity" (PIMs) whose rigid and randomly contorted structures increase high-free volume and surface area while decreasing chain packing efficiently and pore collapse in the solid state [Budd 2004a; Budd 2004b; Budd 2005a; Budd 2005b; McKeown 2005]. Compared to conventional gas separation polymers, the profound significance of these polymers is that they simultaneously display both very high gas permeability and good selectivity, contrary to the normal trade-off behavior of many traditional thermoplastic polymers. These microporous materials are soluble in several common solvents and can be readily fabricated into thin films. Consequently, they have attracted great interest as outstanding membrane materials which have a high potential for gas separation [Budd 2004b; Budd 2005b], adsorption of small molecules such as hydrogen [McKeown 2006b; Ghanem 2007; Budd 2007; McKeown 2007], heterogeneous catalysis [Budd 2003; McKeown 2006c] and as adsorbents for organic compounds [Budd 2003; Maffei 2006].

One important structural feature of PIMs is the presence of kinks in the repeat units. For example, PIM-1, the most studied PIM having a high molecular weight, is prepared from a dioxane-forming reaction between commercially available 5,5',6,6'-tetrahydroxy-3,3,3',3'-tetramethylspirobisindane (TTSBI), and 2,3,5,6-tetrafluoroterephthalonitrile (TFTPN). Although McKeown and Budd suggested several compounds which include a spiro-contorted site as PIMs monomers [McKeown 2006a] there are only a few such monomers reported that provide PIMs for which gas permeabilities have been measured [Ghanem 2008; Carta 2008; Kricheldorf 2006; Budd 2004a]. These few PIMs have been synthesized using a controlled low temperature aromatic nucleophilic substitution polycondensation of tetraphenol monomers with tetrahalogenated monomers containing nitrile or imine electron-withdrawing groups. Among these polymers, they reported the gas permeability coefficients of some ladder polymers such as PIM-1 and PIM-7. PIM-1, is prepared from commercially available 5,5',6,6'-tetrahydroxy-3,3,3',3'-tetramethylspirobisindane (TTSBI) and 2,3,5,6-tetrafluoroterephthalonitrile (TFTPN) by an efficient double aromatic nucleophilic substitution (SNAr) polycondensation.

Few PIM structures with high molecular weight have been reported to date due to the few choices of available monomers and the inability of available monomers to produce sufficiently high molecular weight polymers. The latter is an important consideration in using these materials for membrane gas separation, where materials with high molecular weight are required for coating onto supports and for fabricating free-standing films.

As is well known, the chemical structure and physical properties of membrane materials influence permeability and selectivity [Pandey 2001; Aoki 1999; Dai 2004; George 2001]. Many studies have shown that an improvement in gas transport properties could be obtained by modifying or tailoring the polymer structure. Considerable attention has been devoted to the preparation of new classes of partially fluorinated polymers because of their unusual properties. Trifluoromethyl groups (—$CF_3$) have been reported to significantly improve permeability and selectivity by increasing chain stiffness and reducing interchain interactions such as charge-transfer complexes (CTCs) [Banerjee 1999; Dai 2005]. In addition, —$CF_3$ groups in a polymer backbone serve several other purposes, such as enhancing polymer solubility (commonly referred to as the fluorine effect) without forfeiting thermal stability, lowering dielectric constants and water absorption, increasing the fractional free volume (FFV) of polymers, and increasing glass transition temperature ($T_g$) with concomitant decrease and/or elimination of crystallinity. The phenylsulfonyl group (—$SO_2C_6H_5$) is also a useful group which is employed beneficially in polymers used for gas separation. In general, the sulfonyl group (—$SO_2$—) raises $T_g$ through increasing rigidity of the polymer chain and reduces FFV and permeability, while increasing selectivity [Paul 1994].

Processes for producing PIMs like those produced by Budd and coworkers have been studied under seemingly similar reaction conditions (Kricheldorf 2004). Kricheldorf and coworkers concluded that the majority of the product was cyclic which results in low molecular weight polymer and high polydispersity indices. Further, they found that the use of high temperature or high concentration of reactants, which have previously been shown to favor the decrease of cyclic oligomers, cannot be applied in this reaction due to explosive polycondensation yielding cross-linked product. It is well known that the rate-controlling step in this polycondensation reaction is the dissolution of the monomer salt. The cyclic compounds were formed in the reaction mixture as a result of the high dilution conditions created by poor solubility of the salt. Further, cyclization competes with every chain-growth step at all stages of polycondensation. Further, it has been observed that crosslinking happened quickly when the polymer precipitated from the reaction mixture. Therefore, it is of importance to develop an efficient polycondensation method for preparing PIMs that are substantially free of cyclics and crosslinked structures.

Thus, there is a need in the art to expand the spectrum of high molecular weight PIMs having new structures derived from different monomers for use in membranes having improved gas permeability and separation properties. There is also a need for more efficient processes for producing such polymers.

SUMMARY OF THE INVENTION

In one aspect of the present invention there is provided a polymer of formula (I):

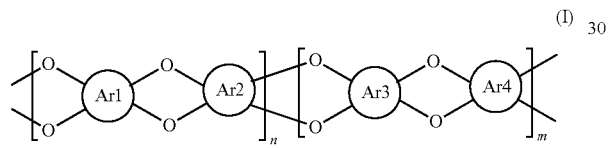

where:

n is an integer from 10 to 5,000; m is an integer from 10 to 5,000;

Ar1 and Ar3 are the same or different and are residues derived from a tetra-hydroxy aromatic monomer, the tetra-hydroxy aromatic monomer being

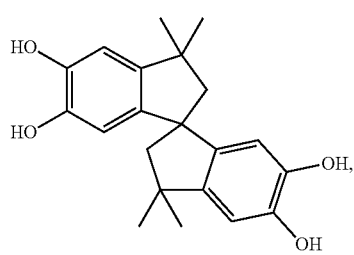

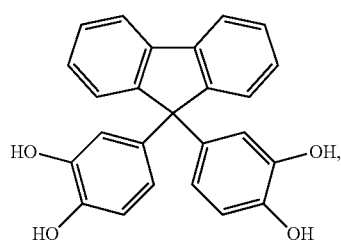

-continued

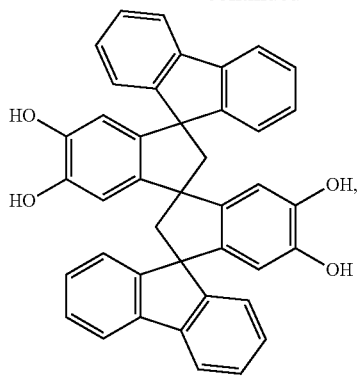

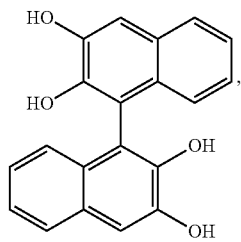

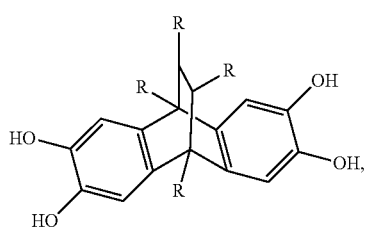

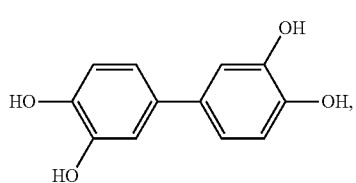

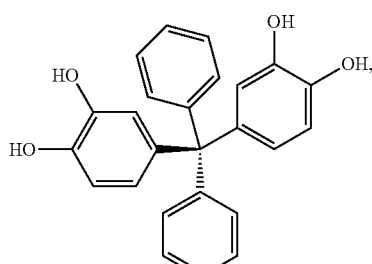 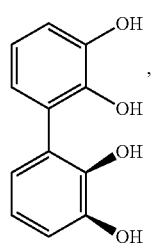

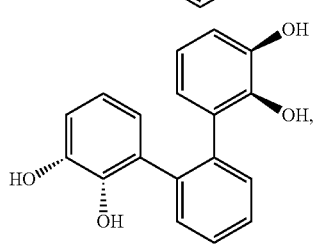

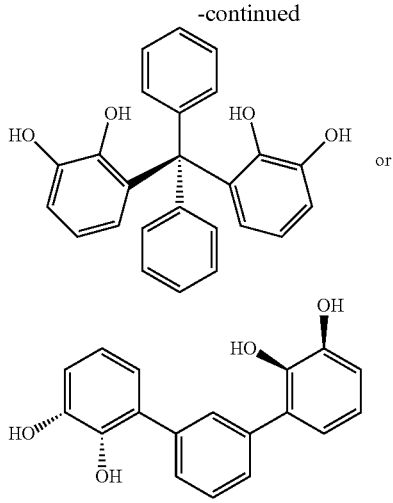

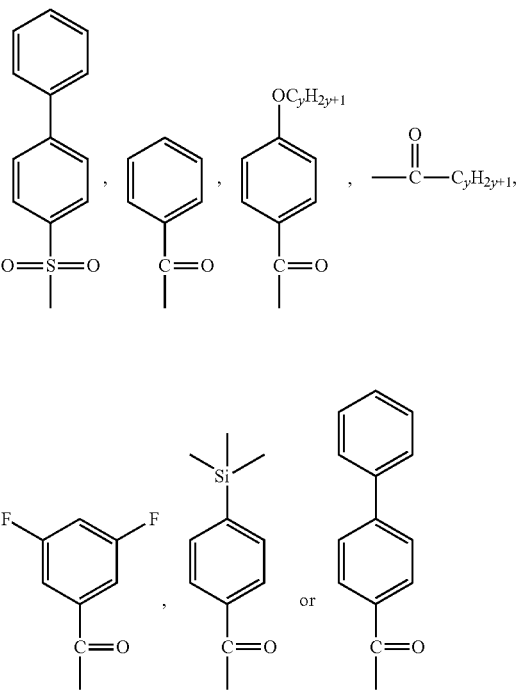

wherein R is the same or different and is H or a $C_1$-$C_8$ alkyl, $C_2$-$C_8$ alkenyl or $C_3$-$C_8$ cycloalkyl group; and, Ar2 and Ar4 are the same or different and are residues derived from a tetra-halogenated aromatic monomer, the tetra-halogenated aromatic monomer being

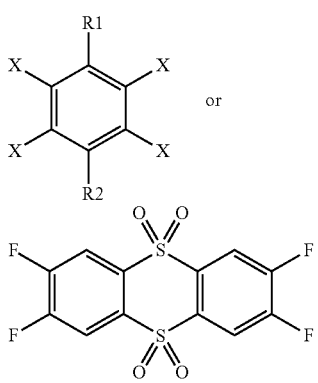

wherein y is an integer from 1 to 8;

with the proviso that when Ar1 is the same as Ar3 and Ar2 is the same as Ar4, R1 and R2 are not both —CN.

Preferably, n is an integer from 40 to 750, more preferably from 40 to 500. Preferably, m is an integer from 40 to 750, more preferably from 40 to 500. The ratio of n:m is preferably in a range of 1:99 to 99:1, more preferably 70:30 to 30:70, for example 50:50. In one embodiment, m=2n. R is preferably H, methyl or ethyl. Ar1 and Ar3 are preferably residues derived from

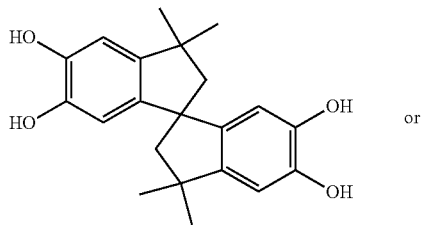

wherein X is F, Cl or Br, and R1 and R2 are the same or different and are

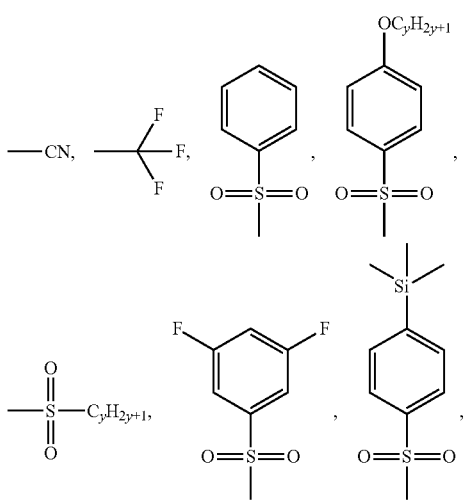

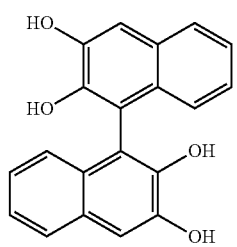

X is preferably F. Preferably, y is an integer from 1 to 4, more preferably y is 1 or 2. Preferably, Ar2 and Ar4 are residues derived from

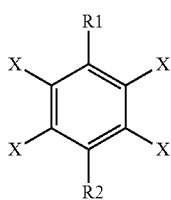

R1 and R2 are the same or different and are preferably

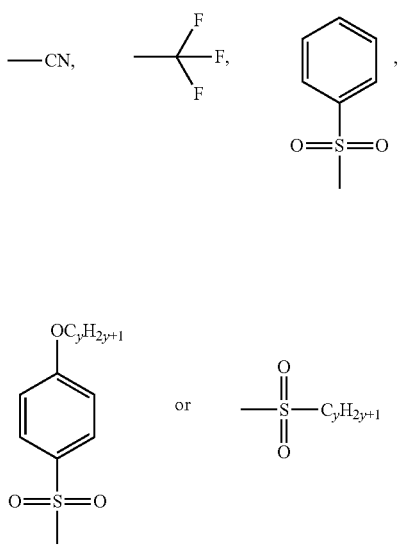

In another aspect of the present invention, there is provided a process for producing a polymer of formula (I) as defined above comprising: contacting one or more tetra-hydroxy aromatic monomers as defined by Ar1 and Ar3 above with one or more tetra-halogenated aromatic monomers as defined by Ar2 and Ar4 above at a temperature in a range of 130-200° C. in a solvent mixture comprising an aprotic polar solvent and a non-polar solvent. The monomers are preferably present in a concentration in a range of 5-50% w/w based on weight of the aprotic polar solvent. Such conditions unexpectedly reduce polymer crosslinking, reduce the quantity of cyclic species formed, increase the yield in a shorter period of time (e.g. complete reaction in under 1 hour), result in higher molecular weight polymers with a narrower molecular weight distribution, result in polymers with improved mechanical properties and increase surface area of the bulk polymer.

Synthesis of Polymers:

Generally, ladder polymers of the present invention may be synthesized by SNAr polycondensation of tetra-hydroxy aromatic monomers with tetra-halogenated aromatic monomers as shown in Scheme 1, wherein Ar1, Ar2, Ar3, Ar4, X, n and m are as defined above.

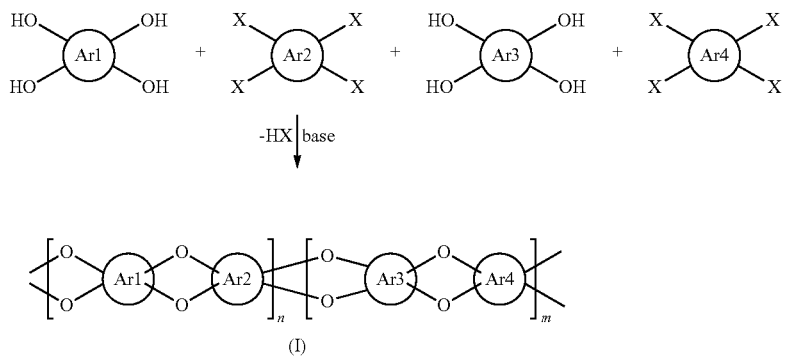

Scheme 1: General Synthesis of PIMs.

When Ar1 is the same as Ar3 and Ar2 is the same as Ar4, the resulting polymer is a homopolymer with [Ar1-Ar2] repeating units. When Ar1 and Ar3 are the same but Ar2 is different from Ar4, the resulting polymer is a copolymer with [Ar1-Ar2]-[Ar1-Ar4] repeating units. When Ar1 and Ar3 are different but Ar2 and Ar4 are the same, the resulting polymer is a copolymer with [Ar1-Ar2]-[Ar3-Ar2] repeating units.

The base may be any suitable base for use in SNAr polycondensation reactions. Aprotic bases are preferred. Some examples of suitable bases include potassium carbonate ($K_2CO_3$), sodium carbonate ($Na_2CO_3$), sodium fluoride (NaF), potassium fluoride (KF) or mixtures thereof. Protic bases, e.g. sodium hydroxide (NaOH), potassium hydroxide (KOH) or mixtures thereof, may be suitable bases if there are no hydrolysable groups (e.g. —CN) on the monomers. The polycondesation is preferably done in an inert atmosphere. The inert atmosphere may comprise gases such as, for example, argon, nitrogen or mixtures thereof. Water and oxygen are preferably excluded as far as possible in the reaction conditions.

The polycondensation is preferably done in a solvent suitable for polycondensation reactions. The solvent is preferably dried to remove water and degassed to remove oxygen. The solvent is preferably an aprotic polar solvent, for example, N,N-dimethylacetamide (DMAc), N'N-dimethylformamide (DMF), dimethylsulfoxide (DMSO), N-methylpyrrolidinone (NMP), sulfolane, diphenylsulfone or mixtures thereof. In one particularly advantageous embodiment, a non-polar solvent is also used in addition to the aprotic polar solvent. The non-polar solvent is preferably benzene, alkylbenzenes (e.g. toluene, xylene, mesitylene), long chain hydrocarbons (e.g. octane), ethyl acetate or mixtures thereof. Benzene, toluene, xylene or mixtures thereof are particularly preferred. The non-polar solvent solubilizes the polymer formed and helps solubilize the monomers in the aprotic polar solvent during the reaction. The non-polar solvent is preferably used in an amount about 2-10 times by volume of the aprotic polar solvent.

Without being held to any particular mode of action, it is known that the rate-controlling step in these type of polycondensation reactions is the dissolution of monomer salts in the aprotic polar solvent. In prior art syntheses of PIMs, cyclic compounds were formed in the reaction mixture as a result of high dilution conditions created by poor solubility of the monomer salt in the aprotic polar solvent. Further, cyclization competes with every chain-growth step at all stages of polycondensation. Further, it has been previously observed that crosslinking happens quickly when the polymer precipitates out from the reaction mixture, therefore the presence of non-polar solvent helps solubilize the polymer reducing the amount of polymer precipitation thereby reducing the amount of crosslinking.

The polycondensation is preferably done at elevated temperature for a period of time suitable to maximize yield. The temperature is preferably in a range of from 50-200° C. The time may be, for example, from less than about 1 hour to as high as 72 hours. In a particularly preferred embodiment, the temperature is in a range of 130-200° C., in particular 150-200° C., for example about 155-160° C., which can reduce the time required to less than one hour. To be able to reach such temperatures without undue crosslinking and/or cyclization, it is advantageous to utilize a non-polar solvent in addition to an aprotic polar solvent. Further, it is advantageous to use a high intensity homogenizer to reduce reaction time even further. Reaction times can be reduced to 15 minutes or less by using such a high intensity homogenizer.

Homopolymers:

When Ar1 and Ar3 are the same, and Ar2 and Ar4 are the same, with the proviso that R1 and R2 are not —CN, the polymer is a homopolymer of formula (II):

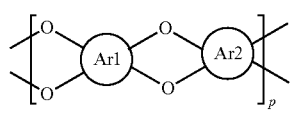

(II)

where p is an integer from 20 to 10,000, and Ar1 and Ar2 are as defined above with the proviso that R1 and R2 are not —CN. Preferably, p is an integer from 40 to 1500, more preferably from 40 to 1000, yet more preferably 40 to 500. Ar2 preferably comprises one or more sulfone (—SO$_2$—) groups, one or more trifluoromethyl (—CF$_3$) groups or a mixture of —SO$_2$— and —CF$_3$ groups. In Ar2, X is preferably F. More preferably, Ar2 comprises two —SO$_2$— groups, or one —SO$_2$— group and one —CF$_3$ group. In particularly preferred embodiments, when Ar2 is a residue derived from

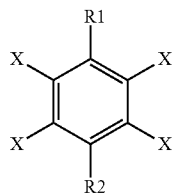

X is F; R1 is —CF$_3$, CH$_3$CH$_2$SO$_2$—, Ph-SO$_2$— or p-CH$_3$O-Ph-SO$_2$—; and, R2 is CH$_3$CH$_2$SO$_2$—, Ph-SO$_2$— or p-CH$_3$O-Ph-SO$_2$—. Ar1 is preferably a residue derived from

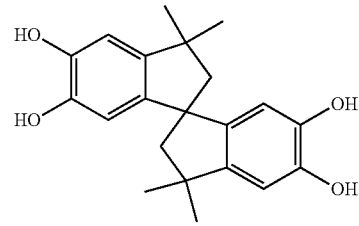 [SMILES: CC1(C)CC2(CC(C)(C)c3cc(O)c(O)cc32)c2cc(O)c(O)cc21]

As discussed previously, certain homopolymeric PIMs have been previously reported. However, the previously reported homopolymers are limited by one or more of low molecular weight, crosslinking, too broad of a molecular weight distribution, difficulty in preparation or scale-up, fixed physical properties (e.g. fixed gas permeabilities and gas pair selectivities, few monomer choices, fewer choices of gas permeability and gas pair selectivity properties, and inability to readily functionalize the main chain structure.

Homopolymeric PIMs of the present invention advantageously extend the possible structures of PIMs, increase gas pair selectivity coupled with a permeability that combines to exceed the Robeson upper bound, increase chemical stability, increase molecular weight, broaden the range of physical properties which are relevant to gas permeability and gas pair selectivity properties, and increase the capability to functionalize the PIM.

Copolymers:

When Ar1 and Ar3, or Ar2 and Ar4, are different, the polymer is a copolymer. Copolymeric PIMs have been hitherto unknown in the art. The copolymers may be random or block copolymers.

In copolymers of the present invention, Ar1, Ar2, Ar3 and Ar4 are as defined above. Ar2, Ar4 or both Ar2 and Ar4 preferably comprise one or more sulfone (—SO$_2$—) groups, one or more trifluoromethyl (—CF$_3$) groups or a mixture of —SO$_2$— and —CF$_3$ groups. In Ar2 and Ar4, X is preferably F. In a particularly preferred embodiment, either Ar2 or Ar4 comprises one or more sulfone (—SO$_2$—) groups, one or more trifluoromethyl (—CF$_3$) groups or a mixture of —SO$_2$— and —CF$_3$ groups, and the other of Ar2 and Ar4 comprises —CN groups. In particularly preferred embodiments, when Ar2 and Ar4 are residues derived from

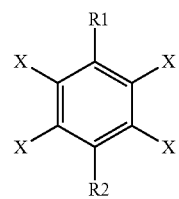

X is F; R1 is —CF$_3$, CH$_3$CH$_2$SO$_2$—, Ph-SO$_2$— or p-CH$_3$O-Ph-SO$_2$— in Ar2; R2 is CH$_3$CH$_2$SO$_2$—, Ph-SO$_2$— or p-CH$_3$O-Ph-SO$_2$— in Ar2; and, R1 and R2 are —CN in Ar4. In another particularly preferred embodiment, one of Ar2 and Ar4 is a residue derived from

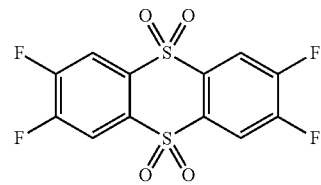

As discussed previously, certain homopolymeric PIMs have been previously reported. However, the previously reported homopolymers are limited by one or more of low molecular weight, crosslinking, too broad of a molecular weight distribution, difficulty in preparation or scale-up, fixed physical properties (e.g. fixed gas permeabilities and gas pair selectivities, few monomer choices, and fewer choices of gas permeability and gas pair selectivity properties.

Copolymeric PIMs (CoPIMs) have one or more of the following advantages: increase in the number of possible structures; increased molecular weight; reduced crosslinking; narrower molecular weight distribution; easier preparation or scale-up; increased thermal and/or chemical stability; tunability of gas permeability and gas pair selectivity properties due to the ability to utilize different ratios of monomers; and, increase in selectivity coupled with a permeability that combines to exceed the Robeson upper bound.

Uses of Polymers:

Polymers of the present invention are useful as materials for gas separation, vapor separation, adsorbents and catalysis. They may be conveniently cast in any suitable form, for example free-standing membranes, dense films, coated films or membranes on support materials (e.g. thin film composite membranes), beads or powders.

Further features of the invention will be described or will become apparent in the course of the following detailed description.

BRIEF DESCRIPTION OF THE DRAWINGS

In order that the invention may be more clearly understood, embodiments thereof will now be described in detail by way of example, with reference to the accompanying drawings, in which:

FIG. 1A depicts chemical structures of various monomers referred to herein;

FIG. 1B depicts chemical structures of PIM-1 and PIM-7;

DESCRIPTION OF PREFERRED EMBODIMENTS

Figure 2:
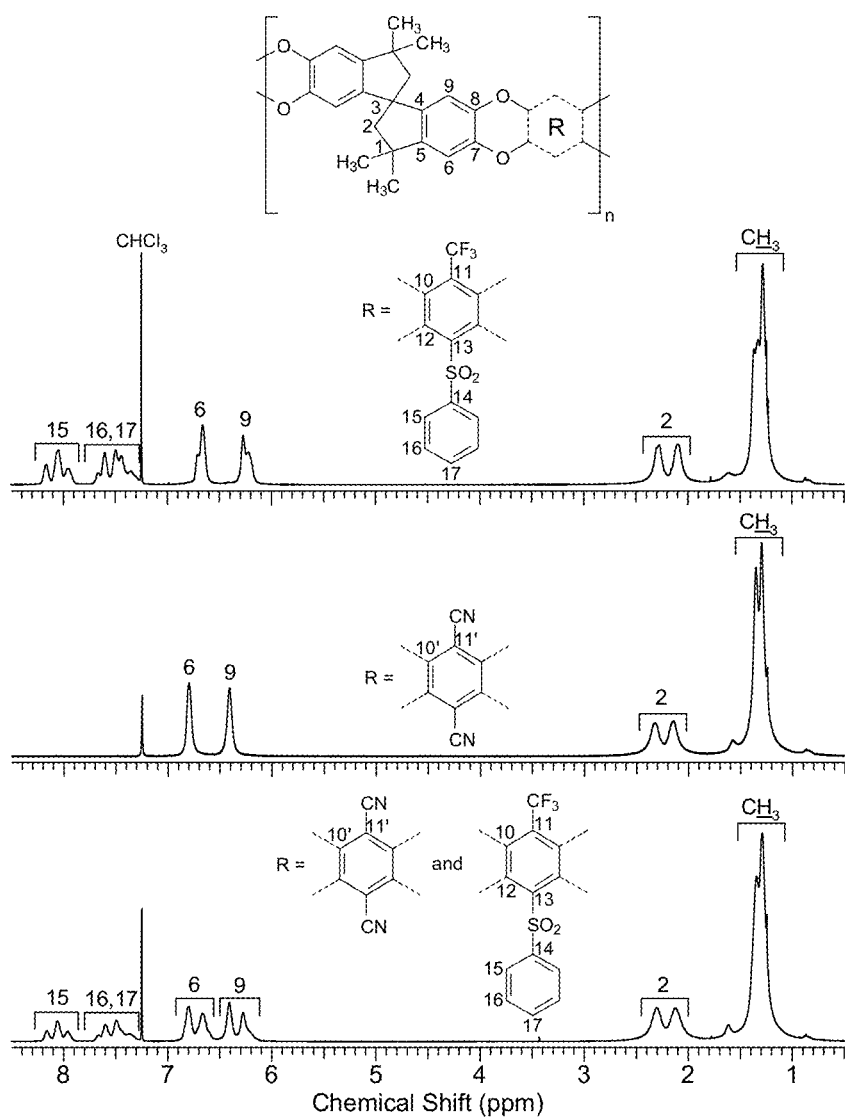
FIG. 2 depicts $^1$H NMR spectra of TFMPSPIM1, TFMPSPIM3 and PIM-1.

Materials:

Hexafluorobenzene (Apollo Scientific Ltd.), 4-methoxylbenzenethiol (Matrix Scientific), 4-Bromo-2,3,5,6-tetrafluorobenzotrifluoride (Matrix Scientific), ethanethiol (Sigma-Aldrich), thiophenol (Sigma-Aldrich), 2,3-naphthalenediol (Sigma-Aldrich), dimethylacetamide (DMAc, Sigma-Aldrich), ferric chloride hexahydrate ($FeCl_3.6H_2O$, Anachemia), sodium hydride (60% NaH dispersion in mineral oil, Sigma-Aldrich), formic acid (Sigma-Aldrich), hydrogen peroxide solution 30% (w/w) in $H_2O$ ($H_2O_2$, Aldrich), anhydrous potassium carbonate ($K_2CO_3$, Sigma-Aldrich), tetrahydrofuran (THF, Aldrich) and toluene (Sigma-Aldrich) were reagent grade and used as received. 5,5',6,6'-Tetrahydroxy-3,3,3',3'-tetramethylspirobisindane (TTSBI, Sigma-Aldrich) was purified by re-crystallization from methanol. Tetrafluoroterephthalonitrile (TFTPN, Matrix scientific) was purified by vacuum sublimation at 150° C. under inert atmosphere. Pyridine (Sigma-Aldrich) was distilled from $CaH_2$.

Characterization Methods:

The structures of the polymeric materials were fully characterized using nuclear magnetic resonance (NMR) spectroscopy. NMR analyses were recorded on a Varian Unity Inova spectrometer at a resonance frequency of 399.961 MHz for $^1$H, 376.276 MHz for $^{19}$F and 100.579 MHz for $^{13}$C. $^1$H and $^{19}$F NMR spectra were obtained from samples dissolved in $CDCl_3$ or DMSO-$d_6$ using a 5 mm pulsed field gradient indirect detection probe. $^1$H-$^{13}$C heteronuclear 2D experiments (HSQC, HMBC) were also obtained from the same indirect detection probe. $^{13}$C NMR spectra were collected using a 5 mm broadband probe. The solvent signals ($CDCl_3$ $^1$H 7.25 ppm, $^{13}$C 77.00 ppm; DMSO-$d_6$ $^1$H 2.50 ppm, $^{13}$C 39.43 ppm) were used as the internal references. An external reference was used for $^{19}$F NMR: $CFCl_3$ 0 ppm.

Molecular weight and molecular weight distributions were measured by GPC using Ultrastyragel™ columns and THF as the eluent at a flow rate of 1 mL/min. The values obtained were determined by comparison with a series of polystyrene standards.

Elemental analysis was carried out with a Thermoquest™ CHNS—O elemental analyzer.

Polymer thermal degradation curves were obtained from thermogravimetric analysis (TGA) (TA Instruments model 2950). Polymer samples for TGA were initially heated to 120° C. under nitrogen gas and maintained at that temperature for 1 h for moisture removal and then heated to 600° C. at 10° C./min for degradation temperature measurement. Glass transition temperatures ($T_g$) were observed from differential scanning calorimetry (DSC) (TA Instruments model 2920), and samples for DSC were heated at 10° C./min under a nitrogen flow of 50 mL/min, then quenched with liquid nitrogen and reheated at 10° C./min for the $T_g$ measurement.

Wide-angle X-ray diffraction (WAXD) was used to investigate d-spacing. A Bruker AXS GADDS instrument was utilized with Co radiation of wavelength (λ) 1.789 Å or Cu Kr radiation of wavelength (λ) 1.54 Å. The value of the d-spacing was calculated by means of Bragg's law (d=λ/2 sin θ), using θ of the broad peak maximum.

Dense polymer films for gas permeability measurements were prepared from 1-2 wt % polymer solutions in chloroform. Polymer solutions were filtered through 0.45 μm polypropylene or poly(tetrafluoroethylene) (PTFE) filters and then cast into either glass or Teflon™ Petri dishes in a glove box and allowed to evaporate slowly for 1 day. The films were soaked in methanol and dried in a vacuum oven at 100° C. for 24 h. The resulting membranes with thickness in the range of 60-80 μm were bright yellow and flexible. The absence of residual solvent in the films was confirmed by weight loss tests using TGA.

Permeability coefficients (P) of $N_2$, $O_2$ and $CO_2$ were determined at 25° C. with a feed pressure of 50 psig and atmospheric permeate pressure using the constant-pressure/variable-volume method. The permeation flow was measured by a mass flow meter (Agilent ADM 2000) or a bubble meter. Permeability (P) was calculated by using a following equation:

$$P = \left(\frac{273}{T}\right) \cdot \left(\frac{dV}{dt}\right) \cdot \left(\frac{l}{\Delta p \cdot A}\right)$$

where dV/dt is the permeate-side flow rate ($cm^3/s$), T is the operation temperature (K) and Δp is the gas pressure differential between the upstream and downstream sides of the membrane. The membrane effective area (A) was 9.6 $cm^2$.

Example 1

Preparation of Heptafluoro-p-Tolylphenylsulfone (HFTPS) Monomer

Into a 50 mL three-necked flask equipped with a magnetic stirrer, an argon inlet and a condenser, thiophenol (2.42 g, 0.022 mol), NaH (0.88 g, 0.022 mol), DMAc (5 mL) were added. The mixture was cooled to −20° C. using an ice salt bath (NaCl/ice=3:1, w:w) and stirred for 1 h. 4-Bromo-2,3,5,6-tetrafluorobenzotrifluoride (5.94 g, 0.02 mol) in 5 mL DMAc was added dropwise, then the temperature was gradually increased to room temperature. After stirring at room temperature for 6 h, the reaction mixture was poured into water and the crude product was washed 3 times. The orange color oil was extracted with chloromethane and dried over $MgSO_4$. After removal of chloromethane, the resulting crude heptafluoro-p-tolylphenylsulfide was oxidized with formic acid (5 mL) and $H_2O_2$ (30%) (6 g) at 50° C. for 2 h, resulting in a white-yellow solid sulfone product that was initially purified by chromatography (using 1/1 v/v dichloromethane/hexane). Pure product in the form of white needle crystals was obtained by recrystallization from hexane. Yield: 65%. Mp: 134° C.

Elem. Anal. Calcd for $C_{13}H_5F_7O_2S$ (358.23 g/mol): C, 43.95%; H, 1.41%; S, 8.95%. Found: C, 43.24%; H, 1.39%; S, 8.95%.

$^1H$ NMR (chloroform-d) δ 8.09 (d, J=8.0 Hz, 2H), 7.73 (t, J=8.0 Hz, 1H), 7.62 (t, J=8.0 Hz, 2H); 19F NMR (chloroform-d) δ −57.6 (t, J=22.5 Hz, 3F), −134.3 (m, 2F), −136.9 (m, 2F). 13C NMR (chloroform-d) δ 145.8-143.0 (d, J=264 Hz, 2H), 145.5-142.7 (d, J=264 Hz, 2H), 139.9 (s, 1H), 135.3 (s, 1H), 129.8 (s, 2H), 128.2 (s, 2H), 125.3-125.0 (t, J=14 Hz, 1H), 124.1-115.9 (q, J=275 Hz, 1H), 114.2-113.9 (m, 1H).

Example 2

Preparation of 2,2'3,3'-Tetrahydroxy-1,1'-Dinaphthyl (THDN) Monomer

A literature procedure was employed [Toda 1989]. A mixture of 2,3-naphthalenediol (16 g, 0.1 mol) and $FeCl_3.6H_2O$ (27 g, 0.2 mol) was finely powdered by agate mortar and pestle. The mixture was then put in a test tube and irradiated with ultrasound at 50° C. for 1 h. Decomposition of the reaction mixture with dilute HCl gave crude 2,2'3,3'-tetrahydroxy-1,1'-dinaphthyl in 85% yield. The tetrol was recrystallized from THF three times to give white needle powder at 53% yield. Mp>300° C.

$^1H$ NMR (DMSO-$d_6$) δ 6.80-6.82 (d, J=8.0 Hz, 2H), 6.94-6.98 (t, J=8.0 Hz, 2H), 7.14-7.18 (t J=8.0 Hz, 2H), 7.24 (s, 2H), 7.64-7.62 (d, J=8.0 Hz, 2H), 8.41 (s, OH), 10.07 (s, OH)

Elem. Anal. Calcd for $C_{20}H_{14}O_4$ (318.32 g/mol): C, 75.46%; H, 4.43% Found: C, 75.41%; H, 4.56%.

Example 3

Preparation of Disulfone Monomers

Three dithioethers were synthesized by modifying known procedures [Kulka 1959; Robson 1963; Langille 1972]. Generally, into a 250 mL three-neck flask equipped with a magnetic stirrer, an argon inlet and a condenser, a thiol (54 mmol), NaH (54 mmol), and dry pyridine (15 mL) were added. The reaction mixture was cooled to −20° C. using an ice salt bath (NaCl:ice=3:1, w/w), and stirred for 1 h. Thereafter, the reaction mixture was added dropwise into hexafluorobenzene (27 mmol) and the temperature was gradually increased to room temperature. After stirring at room temperature for 30 min, the reaction mixture was refluxed for another 20 min and then poured into water. The crude product was washed with 8 N hydrochloric acid and extracted with dichloromethane and dried over $MgSO_4$.

After purifying, the dithioethers (5 g) were oxidized with formic acid (15 mL) and $H_2O_2$ (30%, 20 g) and maintained at 100° C. for 24 h, resulting in white disulfone products, which were collected and purified.

1,2,4,5-Tetrafluoro-3,6-Bisphenylsulfonylbenzene (TFBPSB) Monomer

The dithioether was purified by chromatography (using 1/4, v/v chloromethane/hexane). Pure product in the form of white needle crystals was obtained by recrystallization from hexane. Yield: 48%. Mp: 109-110° C.

Elem. Anal. Calcd for $C_{18}H_{10}F_4S_2$ (366.4 g/mol): C, 59.01%; H, 2.75%; S, 17.5%. Found: C, 58.51%; H, 2.69%; S, 17.62%.

$^1H$ NMR (chloroform-d) δ 7.43-7.39 (m, 4H), 7.35-7.29 (m, 6H). $^{19}F$ NMR (chloroform-d) δ −132.4 (s, 4F). $^{13}C$ NMR (chloroform-d) δ 146.9 (d, J=251 Hz), 132.5 (s), 131.0 (s), 129.4 (s), 128.1 (s), 115.3 (m).

After oxidation, the raw TFBPSB disulfone monomer was recrystallized from dimethylformamide (DMF), to give white needle crystals in a yield of 81%. Mp>300° C.

Elem. Anal. Calcd for $C_{18}H_{10}F_4O_4S_2$ (430.39 g/mol): C, 50.23%; H, 2.34%; S, 14.9%. Found: C, 49.57%; H, 2.042%; S, 14.89%.

$^1H$ NMR (DMSO-$d_6$) δ 8.03 (d, J=8.0 Hz, 4H), 7.85 (t, J=8.0 Hz, 2H), 7.71 (t, J=8.0 Hz, 4H). $^{19}F$ NMR (DMSO-$d_6$) δ −135.6 (s, 4F). $^{13}C$ NMR (DMSO-$d_6$) δ 145 (dm, J=256 Hz), 139.2 (s), 135.6 (s), 129.9 (s), 127.7 (s), 124.2 (m).

1,2,4,5-Tetrafluoro-3,6-Bis(Methoxy-4-Phenylsulfonyl)Benzene (TFBMPSB) Monomer

The dithioether was purified by chromatography (using 1/2, v/v chloromethane/hexane). Pure product in the form of white flake crystals was obtained by recrystallization from hexane. Yield: 51%. Mp: 104° C.

Elem. Anal. Calcd. for $C_{20}H_{14}F_4O_2S_2$ (426.45 g/mol): C, 56.33%; H, 3.31%; S, 15.04%. Found: C, 55.30%; H, 3.04%; S, 15.01%.

$^1$H NMR (chloroform-d) δ 7.46 (d, J=8 Hz, 4H), 6.84 (d, J=8 Hz, 4H), 3.80 (s, 6H). $^{19}$F NMR (chloroform-d) δ −133.7 (s, 4F). $^{13}$C NMR (chloroform-d) δ 160.2 (s), 146.7 (dm, J=251 Hz), 134.8 (s), 122.4 (s), 114.8 (s), 109.8 (m), 55.3 (s).

After oxidation, the crude TFBMPSB disulfone monomer was recrystallized from DMF, to give white needle crystals in 78% yield. Mp>300° C.

Elem. Anal. Calcd. for $C_{20}H_{14}F_4O_6S_2$ (490.45 g/mol): C, 48.98%; H, 2.88%; S, 13.08%. Found: C, 48.38%; H, 3.047%; S, 13.01%.

$^1$H NMR (DMSO-$d_6$) δ 7.95 (dd, J=8 Hz, 4H), 7.20 (dd, J=8 Hz, 4H), 3.86 (s, 6H). $^{19}$F NMR (DMSO-$d_6$) δ −136.2 (s, 4F). $^{13}$C NMR (DMSO-$d_6$) δ 161.3 (s), 144.5 (dm, J=251 Hz), 133.3 (s), 130.3 (s), 123.1 (m), 115.2 (s), 54.91 (s).

1,2,4,5-Tetrafluoro-3,6-Bis(Ethylsulfonyl)Benzene (TFBESB) Monomer

The 1,4-bis(ethylthio)-2,3,5,6-tetrafluorobenzene was oxidized without purification. The crude disulfone was recrystallized in DMF and toluene to give white needles of TFBESB disulfone monomer in 72% yield. Mp: 239° C.

Elem. Anal. Calcd. for $C_{10}H_{10}F_4O_4S_2$ (334 g/mol): C, 35.93%; H, 3.02%; S, 19.18%. Found: C, 35.65%; H, 2.91%; S, 18.65%.

$^1$H NMR (DMSO-$d_6$) δ 3.61 (q, J=8 Hz, 4H), 1.27 (t, J=8 Hz, 6H). $^{19}$F NMR (DMSO-$d_6$) δ −135 (s, 4F). $^{13}$C NMR (DMSO-$d_6$) δ 142.4 (dm, J=251 Hz), 129.94 (m), 51.2 (s), 6.4 (s).

Example 4

Preparation of 2,3,7,8-Tetrafluoro-5,5',10,10'-Tetraoxidethianthrene (TFTOT) Monomer 2,3,7,8-tetrafluorothianthrene was synthesized by modifying a known procedure [Bock 1982]. Thus, into a 250 mL three-neck flask equipped with a magnetic stirrer, an argon inlet and a condenser, difluorobenzene (20 mmol), $AlCl_3$ (60 mmol), and dry dichloromethane (50 mL) were added. The reaction mixture was cooled to 0-20° C. using an ice salt bath (NaCl:ice=3:1, w/w), and stirred for 1 h. Thereafter, the reaction mixture was added dropwise into $S_2Cl_2$ (20 mmol) and the temperature was gradually increased to room temperature. After stirring at room temperature for 2 hour, the reaction mixture was refluxed for another 20 min and then poured into water. The crude product was washed with 8 N hydrochloric acid and extracted with dichloromethane and dried over $MgSO_4$. After removed the dichloromethane, the 2,3,7,8-tetrafluorothianthrene (5 g) was recrystallized from hexane to give white needle crystals in a yield of 49%. Mp=108° C.

$^1$H NMR (chloroform-d) δ 7.309 (t, J=8.0 Hz, 4H). $^{19}$F NMR (chloroform-d) δ −136.4 (s, 4F). $^{13}$C NMR (chloroform-d) δ 150.07 (dd, J=252 Hz), 131.34 (t, J=5.3 Hz), 117.64 (m).

To synthesize the TFTOT monomer, 20 g of 2,3,7,8-tetrafluorothianthrene was oxidized with formic acid (100 mL) and $CrO_3$ (excess) and maintained at 100° C. for 24 h, resulting in white 2,3,7,8-tetrafluoro-5,5',10,10'-tetraoxidethianthrene (TFTOT), which were collected and recrystallized from DMF to give white flake crystals in a yield of 92%. Mp>300° C.

Elem. Anal. Calcd for $C_{12}H_4F_4O_4S_2$ (352.28 g/mol): C, 40.91%; H, 1.14%; S, 18.20%. Found: C, 41.13%; H, 1.09%; S, 18.26%.

$^1$H NMR (DMSO-$d_6$) δ 8.087 (t, J=8.0 Hz, 4H). $^{19}$F NMR (DMSO-$d_6$) δ −123.185 (t, J=8.0 Hz, 4F).

Example 5

Preparation of PIM-1 Using a Process of the Present Invention

Into a 100 mL three-necked flask equipped with a magnetic stirrer, an argon inlet, and a Dean-Stark trap, TFTPN (2.001 g, 0.01 mol) and TTSBI (3.404 g, 0.01 mol), anhydrous $K_2CO_3$ (4.14 g, 0.03 mol), DMAc (20 mL), and toluene (10 mL) were added. During the initial 20-30 minutes, a small amount of water was observed in the Dean-Stark trap. The mixture was refluxed at 160° C. for 40 min, and then the viscous solution was poured into methanol. A yellow flexible threadlike polymer was obtained. The polymer product was dissolved into chloroform and re-precipitated from methanol. The resulting polymer was refluxed for several hours with deionized water, and dried at 100° C. for 48 h.

Example 6

Comparison of PIM-1 Properties for PIM-1 Polymers Produced by a Process of the Present Invention and by a Prior Art Process PIM-1 polymers were produced using a standard prior art procedure (Budd 2004a] and a procedure in accordance with the present invention. Reaction conditions are shown in Table 1. Various physical properties of the PIM-1 polymers produced were determined and are shown in Table 2. It is evident from Table 2 that the process of the present invention results in polymers having larger $M_n$, which is advantageous for materials for gas separation membranes, Further, as evidenced by the $M_w/M_n$ ratio, PIM-1 polymers produced by the present invention have less cyclic and cross-linked fractions. Furthermore, mechanical properties like tensile stress and strain are improved in PIM-1 polymers produced by the process of the present invention. Finally, PIM-1 polymers produced by the present process have enhanced surface area ($S_{BET}$).

TABLE 1

Reaction conditions for PIM-1 polymer production

| Condition | Budd 2004a | Present Invention |
|---|---|---|
| Temperature | 65° C. | 155° C. |
| TTSBI:TFTPN:$K_2CO_3$ | 1:1:2.05 | 1:1:3 |
| Aprotic polar solvent | DMAc | DMAc |
| TTSBI:Aprotic polar solvent | 1 mol:7 mL | 1 mmol:2 mL |
| TTSBI:Toluene | 1 mol:0 mL | 1 mmol:6 mL |
| Time | 72 h | 45-60 min |

TABLE 2

Properties of PIM-1 polymers produced by different processes

| | PIM-1 from Budd 2004a | PIM-1 from Present Invention |
|---|---|---|
| $M_n$ | 54,000 | 71,000 |
| $M_w$ | 473,000 | 142,000 |

TABLE 2-continued

Properties of PIM-1 polymers produced by different processes

|  | PIM-1 from Budd 2004a | PIM-1 from Present Invention |
| --- | --- | --- |
| $M_w/M_n$ | 8.7 | 2.0 |
| Yield (%) | 80 | 90 |
| Tensile stress at break (MPa) | — | 47.6 |
| Tensile strain at break (%) | — | 13.7 |
| $S_{BET} (m^2 g^{-1})$ | ~700 | 780 |

Example 7

Preparation and Characterization of PIM Ladder Polymers Containing Trifluoromethyl and Phenylsulfone Side Groups (TFMPSPIM1-4)

A series of TFMPSPIM ladder polymers 1-4 were synthesized by polycondensation of TTSBI, HFTPS and TFTPN (with the molar ratio 1:1:0; 3:2:1; 2:1:1; 3:1:2) using a procedure similar to that of Example 5, and illustrated in Scheme 2.

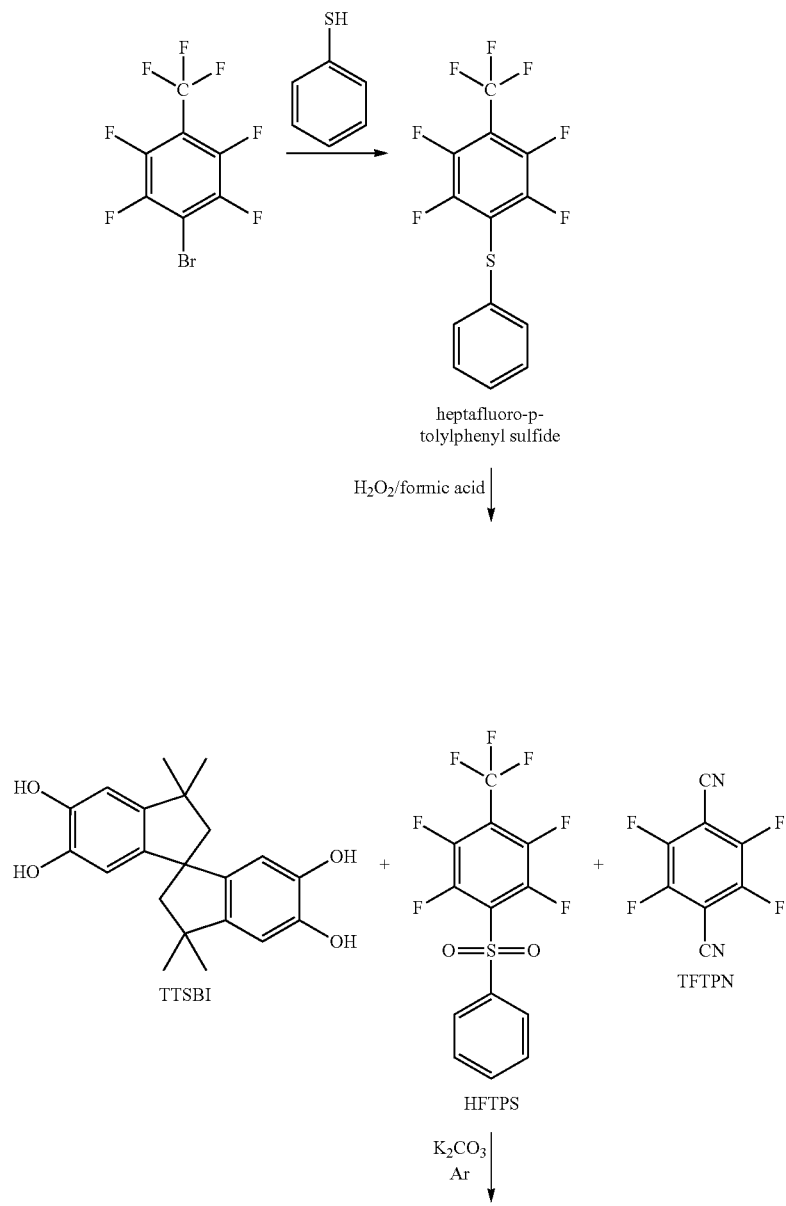

Scheme 2: Synthesis of TFMPSPIM1-4

-continued

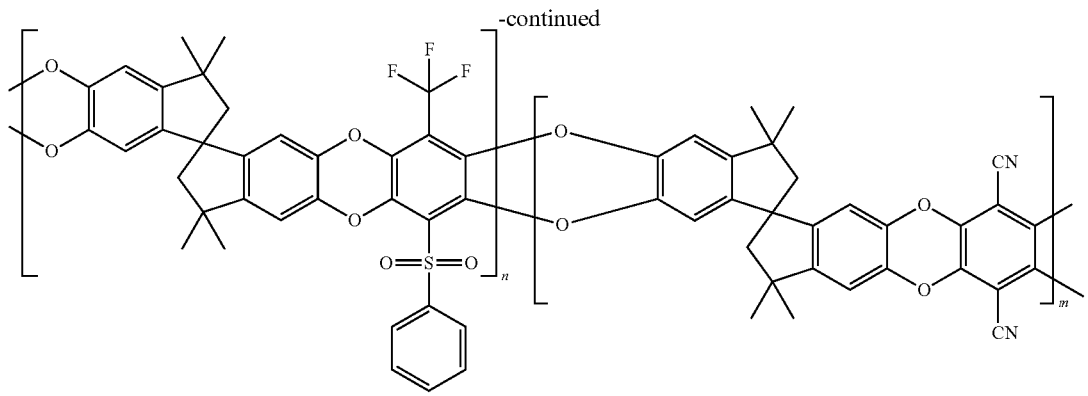

Monomer Synthesis

Alsop et al. previously reported the synthesis of HFTPS by oxidation of heptafluoro-p-tolylphenylsulfide, obtained from the reaction of thiophenol with octafluorotoluene [Alsop 1962]. As far as we are aware, HFTPS has not previously been utilized as a monomer in a polymerization reaction. The present synthetic method is different from the previous report and comprises two steps as shown in Scheme 2. In the first step, the bromine atom in 4-bromo-2,3,5,6-tetrafluorobenzotrifluorde is displaced by thiophenol using NaH at −20° C.

Both F-Ar and Br-Ar react with thiophenols under basic conditions by aromatic nucleophilic substitution reaction, but the reactivity is different. At higher temperatures, F-Ar is more reactive, while at lower temperatures, Br-Ar is more easily displaced, since —Br is an efficient leaving group specifically for reactions with thiophenolates. Elevated temperatures (above 60° C.) or longer reaction times would lead to more byproducts, indicating that the comparative selectivity of thiophenol group decreases. $K_2CO_3$ can be also used as a base for this reaction at these conditions. However, at lower temperatures, water cannot be removed and it continues to react with Ar-F to form Ar-OH, thereby reducing the yield. A small amount of $CaH_2$ was added to the reaction at the beginning to eliminate the water efficiently. Although the resulting $Ca(OH)_2$ was basic, it does not react readily with F-Ar at low temperature due to the poor solubility. The crude product was oxidized without purification. The thioether could be completely converted to sulfone using excess $H_2O_2$ in a heterogeneous formic acid suspension at 50° C. within 2 hours. In terms of its use as a monomer for ladder polymers, the new monomer relies on the electron withdrawing power of sulfone, rather than nitrile used in the synthesis of PIM-1.

Polymerization

The ladder PIMs (including TFMPSPIM and PIM-1) containing —$CF_3$, —$SO_2C_6H_5$, and —CN groups, were synthesized by SNAr polycondensation using various feed ratios of TTSBI/HFTPS/TFTPN, so that polymers with different molar percentages of —CN and —$CF_3$/—$SO_2C_6H_5$ (Scheme 2) were obtained. The ideal structures of the ladder polymers are linear chains without crosslinking. The characterization results are listed in Table 3. The polymers are named TFMPSPIM1-4, where PIM stands for polymer of intrinsic microporosity, TFM and PS refers to trifluoromethyl and phenylsulfonyl respectively.

TABLE 3

Physical Properties of TFMPSPIM1-4 and PIM-1

| Polymers | TTSBI (molar ratio) | HFTPS (molar ratio) | TFTPN (molar ratio) | $M_n$ | $M_w$ | $M_w/M_n$ | Tensile stress at break (MPa) | Tensile strain at break (%) |
|---|---|---|---|---|---|---|---|---|
| TFMPSPIM1 | 1 | 1 | 0 | 77,000 | 156,000 | 2.0 | 33.6 | 3.9 |
| TFMPSPIM2 | 3 | 2 | 1 | 71,000 | 143,000 | 2.0 | 38.3 | 4.4 |
| TFMPSPIM3 | 2 | 1 | 1 | 66,000 | 139,000 | 2.1 | 43.3 | 5.2 |
| TFMPSPIM4 | 3 | 1 | 2 | 64,000 | 110,000 | 1.7 | 46.2 | 5.6 |
| PIM-1 | 1 | 0 | 1 | 55,000 | 85,000 | 1.6 | 47.1 | 11.2 |

Figure 4:
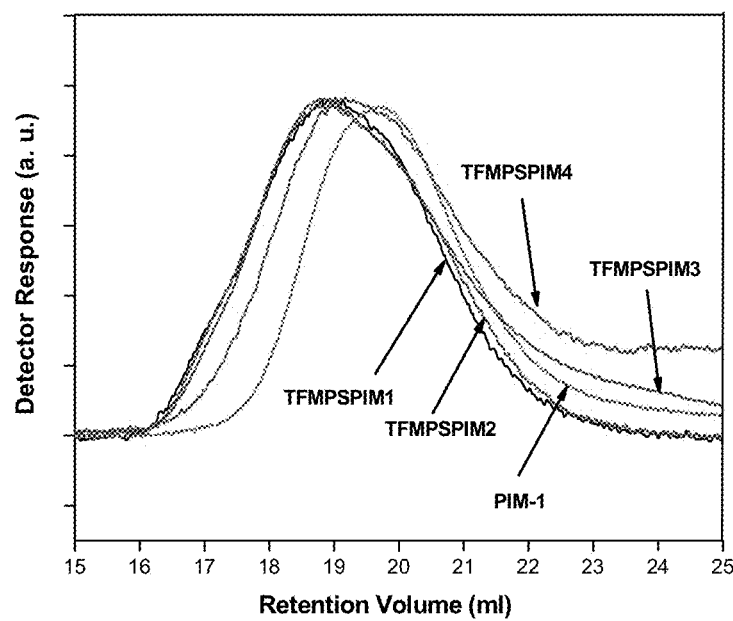
FIG. 4 depicts GPC curves for TFMPSPIM1-4 and PIM-1.

The synthesis of ladder polymers with substantially reduced amounts of cyclic species or crosslinking was accomplished using new polymerization conditions applied to PIMs. A higher polymerization temperature of 160° C. and higher monomer concentrations (monomer:solvent=1 mmol:2 mL) in DMAc were used compared with the previously reported polymerization conditions conducted at lower temperatures. DMAc is largely compatible with both the monomer salts and growing polymer chain at this temperature. In addition, excess toluene (toluene:DMAc=4:1 v/v) was introduced into the reaction not only to remove generated water, but to provide solubility enhancement of the polymer. In a similar reaction carried out in the absence of excess toluene, crosslinked polymer formed readily in the latter stages of polymerization (approx. the last 10 min). The new high-temperature polymerization procedure for PIM-1 reported here led to high molecular weight polymers within 40 min. Compared with the originally reported PIM synthesis [Budd 2004b], the reaction conditions reported here require less time and the explosion-like polycondensation is relatively easy to control. In contrast, with typical nucleophilic aromatic substitution polycondensation reactions to produce poly(aryl ether)s, the formation of the ladder polymers is more complicated. As shown in Scheme 1 and Scheme 2, each monomer has four reactive groups, greatly increasing the susceptibility for crosslinking to occur. However, using the present reaction conditions, GPC results (Table 3) show that high molecular weight polymers ($M_n$>55,000 Da) were obtained and the polydispersity index is approximately 2.0, which is consistent with the results of typical polycondensation reactions in which each monomer has two reactive sites. On GPC curves (FIG. 4), there is no shoulder peak in the low or high molecular weight region around the main peak, indicating that it is a clean reaction with few crosslinked or cyclic structures. GPC results also showed that TFMPSPIM1-4 polymers with higher molecular weight as compared to PIM-1 were obtained under the same reaction condition. The $M_n$ of the polymer decreased as the ratio of monomer HFTPS in the copolymer was reduced. The homopolymer prepared from HFTPS had the highest $M_n$, while PIM-1 homopolymer had the lowest. A plausible explanation is that the —$CF_3$ group and —$SO_2C_6H_5$ enhance the solubility of the polymer and growing chain, so that the polymer chains are unfolded, uncoiled and unpacked, and the chain-growth step reaction is facilitated. Meanwhile, the —F and —OH on neighboring aromatic rings readily react with each other and form ladder structures with less propensity for crosslinking.

The mechanical properties of the ladder polymer series are listed in Table 3. Tensile stress at break and tensile strain at break decreased due to the introduction of increasing amounts of —$CF_3$ and —$SO_2C_6H_5$ into the polymer chain. In the series from PIM-1 to TFMPSPIM4, tensile strain at break drops off sharply from 11.2% to 5.6% while almost maintaining the same tensile stress at break (from 47.1 to 46.2 MPa), which implies that the polymer had additional rigidity due to the introduction of pendant —$CF_3$ and —$SO_2C_6H_5$ groups.

NMR Analysis

Figure 3:
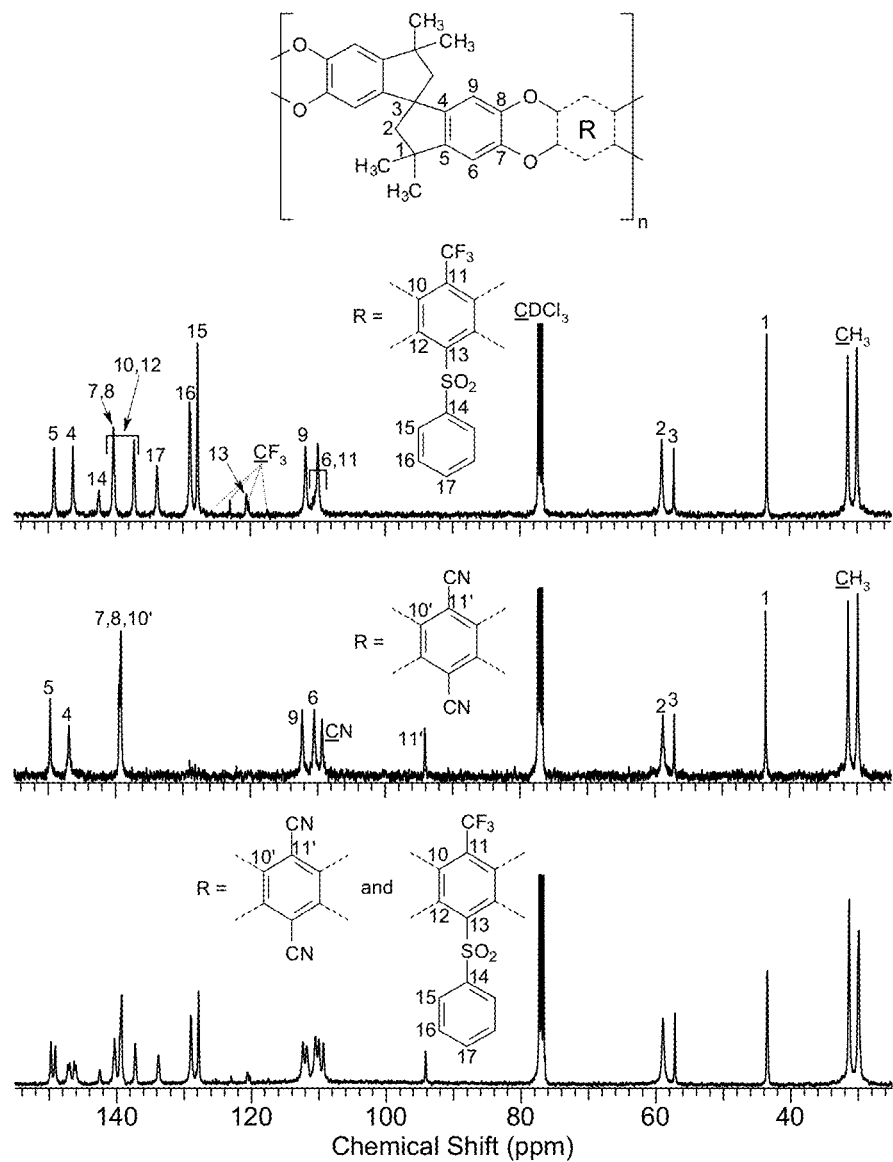
FIG. 3 depicts $^{13}$C NMR spectra of TFMPSPIM1, TFMPSPIM3 and PIM-1.

The TFMPSPIM1 and PIM-1 homopolymers and TFMPSPIM2-4 copolymers were fully characterized by $^1$H, $^{13}$C and $^{19}$F NMR spectroscopy ($^{19}$F NMR (chloroform-d) −56.2 ppm (s, 3F)). Carbon NMR was particularly useful as there are many quaternary carbon atoms on these polymers. Stacked $^1$H NMR spectra of TFMPSPIM1, PIM-1 and TFMPSPIM3 are displayed in FIG. 2 while $^{13}$C spectra of the same polymer series are displayed in FIG. 3. The aliphatic and aromatic hydrogen signals of PIM-1 and TFMPSPIM1 were unambiguously assigned with the help of 2D HSQC and HMBC. Long range C—H correlations involving C1 with $CH_3$ (2JC-C—H) and H6 (3JC-C—C—H) helped differentiate the H6 signal from H9. Most PIM-1 carbon signals were assigned using direct HSQC C—H couplings. All the quaternary carbon atom signals from the TTSBI monomer part were identified by multiple bonds C—H correlations (HMBC) with previously assigned proton frequencies. The absence of hydrogen atoms on the TFTPN monomer results in no signals in 2D HSQC, HMBC NMR. Therefore C10', C11' and —CN were assigned based on their chemical shifts. C10' is strongly deshielded by the electronegative oxygen atom and was therefore easily assigned as the signal at the highest frequency (139 ppm). On the other hand, C11' is shielded by the electron donating effect through delocalization of the same oxygen atoms. C11' is sandwiched between two C—O groups and will therefore be strongly shielded and shifted to very low frequencies hence the peak at 94 ppm. The last quaternary carbon, —CN, appears in the typical —CN range (109 ppm). A $^{13}$C NMR prediction spectrum was obtained (ACD Labs prediction software, v. 10.04, December 2006) in order to compare the actual and predicted chemical shifts for C10', C11' and CN. The predicted chemical shifts were within 2 ppm for C10' and C11' and within 7 ppm for CN, hence validating our peak assignments based on NMR knowledge. The $^1$H and $^{13}$C NMR spectra of TFMPSPIM1 homopolymer were obviously similar to those of PIM-1 homopolymer due to their identical TTSBI monomer residue within the backbone. The additional signals arising from the new monomer were readily assigned in both $^1$H and $^{13}$C NMR with the help of 2D HMBC and HSQC. As before, the C—O carbon atoms C10' and C12' were assigned to high frequencies (137-141 ppm). The —$CF_3$ and C11' were identified by their spin-couplings with the $^{19}$F atoms (1JC-F=277 Hz, 2JC11'-F≈30 Hz). The $^1$H and $^{13}$C NMR spectra of the copolymer TFMPSPIM3 prepared from the monomer ratio 2 TTSBI:1 HFTPS:1 TFTPN are shown as the lower spectra in FIGS. 2 and 3. As expected, these spectra display the same characteristics as the two fully characterized homopolymers PIM-1 and TFMPSPIM1. The specific low frequency (94 ppm) C11' of PIM-1 and the specific quartet —$CF_3$ of TFMPSPIM1 are clearly visible in the $^{13}$C NMR spectrum. Furthermore, the experimental ratio of intensity values for proton H-15, 16, 17 compared with H-6, 9 is exactly 5H: 8H, as expected for two repeat units of the TFMPSPIM3 copolymer. Finally, the $^{19}$F NMR spectra (not shown) were collected for all three polymers. Only TFMPSPIM1 and TFMPSPIM3 showed a signal at ca. 56 ppm which is characteristic of a —$CF_3$ group. It is worthwhile mentioning that no aromatic F signal was observed.

Thermal Analysis

Thermal analyses for TFMPSPIM and PIM-1 were carried out and the results are summarized in Table 4. All the polymers have no discernable $T_g$ in the measured range of 50° C. to 350° C. TGA experiments showed that all the polymers have excellent thermal stabilities and the actual onset temperature of decomposition in nitrogen is above 350° C. There is also some trend between this temperature and monomer ratio. Generally, nitrile-containing polymers have high thermal stability, likely due to strong dipolar interactions. Table 4 shows that with increasing molar content of —CN in the polymers, the onset of thermal decomposition also increased. However, TFMPSPIM homopolymer and copolymers all showed very good thermal stability even after the replacement of nitrile with —$CF_3$ and pendant —$SO_2C_6H_5$ groups.

TABLE 4

Thermal Properties of TFMPSPIM1-4 and PIM-1

| Polymers | $T_d$ (° C.)$^a$ | $T_d$ (° C.)$^b$ | $T_{d5}$ (° C.)$^c$ | RW (%)$^d$ |
|---|---|---|---|---|
| TFMPSPIM1 | 352.8 | 430.3 | 437.7 | 59.15 |
| TFMPSPIM2 | 357.6 | 450.9 | 458.5 | 62.82 |
| TFMPSPIM3 | 368.3 | 463.5 | 468.3 | 63.04 |
| TFMPSPIM4 | 370.9 | 482.8 | 486.8 | 64.79 |
| PIM-1 | 429.6 | 492.6 | 495.4 | 68.17 |

$^a$Actual onset temperature of decomposition.
$^b$Extrapolated onset temperature of decomposition measured by TGA.
$^c$Five percent weight loss temperature measured by TGA
$^d$Residue weight at 600° C. under N2.

X-Ray Diffraction Studies

Fractional free volume (FFV) increased with increasing nitrile content, suggesting that TFMPSPIMs with increasing —$CF_3$ and —$SO_2C_6H_5$ pendant groups pack interchain space more efficiently than PIM-1, as shown in Table 5.

TABLE 5

Physical Properties of TFMPSPIM1-4 and PIM-1 from X-ray Studies

| Polymers | d-space Å | ρ g/cm³ | $V_{sp}$ cm³/g | M g/mol | $V_w$ cm³/mol | $V_f$ cm³/g | FFV |
|---|---|---|---|---|---|---|---|
| TFMPSPIM1 | 6.30 | 1.214 | 0.82 | 618.62 | 304.4 | 0.180 | 0.22 |
| TFMPSPIM2 | 6.34 | 1.196 | 0.84 | 565.90 | 285.0 | 0.185 | 0.22 |
| TFMPSPIM3 | 6.50 | 1.156 | 0.87 | 539.55 | 275.4 | 0.206 | 0.24 |
| TFMPSPIM4 | 6.60 | 1.089 | 0.91 | 513.20 | 265.7 | 0.237 | 0.26 |
| PIM-1 | 6.88 | 1.063 | 0.94 | 460.48 | 246.3 | 0.244 | 0.26 |

The disruption in chain packing is validated by FFV and was calculated using the following relationship [Lee 1980]:

$$V_f = (V_{sp} - 1.3 V_w)$$

$$FFV = V_f / V_{sp}$$

where $V_f$ is the free volume, $V_{sp}$ is the specific volume. Membrane samples had a density in the range 1.06-1.21 g cm³, as determined by measurements of their weight in air and in ethanol. $V_w$ is the specific van der Waals volume calculated using the group contribution method of Bondi [Bondi 1964; van Krevelen 1990].

Figure 5:
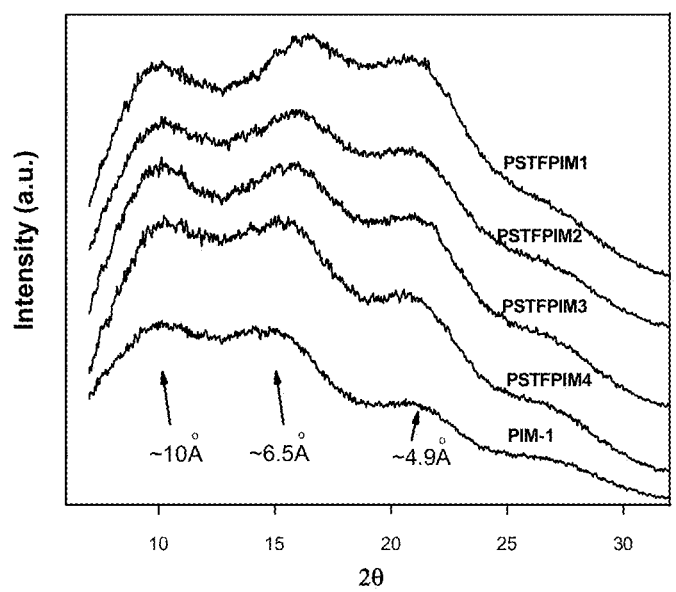
FIG. 5 depicts WAXD of TFMPSPIM1-4 and PIM-1.

These assumptions are supported by the X-ray diffraction measurements shown in FIG. 5, which reveal that all the polymers were amorphous. Three broad peaks were observed for all polymers. The peak at higher angles (4.9 Å) can be attributed to the chain-to-chain distance of space efficiently packed chains. The second peak, corresponding to more loosely packed polymer chains with a d-spacing of about 6.50 Å, is attributed to polymers maintaining their conformation with micropores between the chains [Weber 2007]. The exact d-spacing values were calculated from WAXD spectra by Bragg's law and are listed in Table 5. These values are consistent with the explanation of the free volume theory. The d-spacing of TFMPSPIM1 homopolymer is about 6.30 Å and it becomes larger with decreasing molar amounts of —$CF_3$ and —$SO_2C_6H_5$ groups in the main chain, suggesting that the —$CF_3$ and —$SO_2C_6H_5$ pendant groups affect the polymer chain packing and decrease polymer d-spacing, possibly by inter-chain space-filling. The third peak at a d-spacing of about 10 Å corresponds to the distance between the spiro-carbon atoms, which is about 10-15 Å for PIM-1 and is very similar to the calculated distances for TFMPSPIM1-4. The significance of the distance between the spiro-carbon centers is that the relatively planar rigid chain segments change direction and are skewed at these points, preventing efficient chain packing.

Pure-Gas Permeation Properties

A tradeoff relationship is usually observed between permeability (P) and ideal selectivity (α) for common gases in glassy or rubbery polymers, i.e., higher permeability is gained at the cost of lower selectivity and vice versa. Upper bound performance lines for the relationship between gas permeability and selectivity have been proposed by Robeson [Robeson 1991]. Pure-gas permeability coefficients (P) were measured on dense films (PIM-1, TFMPSPIM1-4) for $O_2$, $N_2$, and $CO_2$ and a summary of these P values and ideal selectivities for various gas pairs are shown in Table 6. As can be seen in Table 6, TFMPSPIM1-4 were significantly more selective than PIM-1 for all gases.

TABLE 6

Gas Permeabilities and Ideal Selectivities of TFMPSPIM1-4 and PIM-1

| Polymers | P (Barrer[a]) | | | Selectivity α[b] | |
|---|---|---|---|---|---|
| | $O_2$ | $N_2$ | $CO_2$ | $O_2/N_2$ | $CO_2/N_2$ |
| TFMPSPIM1 | 156 | 33 | 731 | 4.7 | 22 |
| TFMPSPIM2 | 308 | 75 | 1476 | 4.1 | 20 |
| TFMPSPIM3 | 561 | 158 | 2841 | 3.6 | 18 |
| TFMPSPIM4 | 737 | 217 | 3616 | 3.4 | 17 |
| PIM-1 | 1133 | 353 | 5366 | 3.2 | 15 |
| PIM-1[11] | 370 | 92 | 2300 | 4.0 | 25 |
| PIM-1[24] | 786 | 238 | 3496 | 3.3 | 14.7 |

[a] Permeability coefficients measured at 25° C. and 50 psig feed pressure. 1 Barrer = $10^{-10}$ [cm³ (STP) · cm]/(cm² · s · cmHg).
[b] Ideal selectivity α = (Pa)/(Pb).

Figure 6:
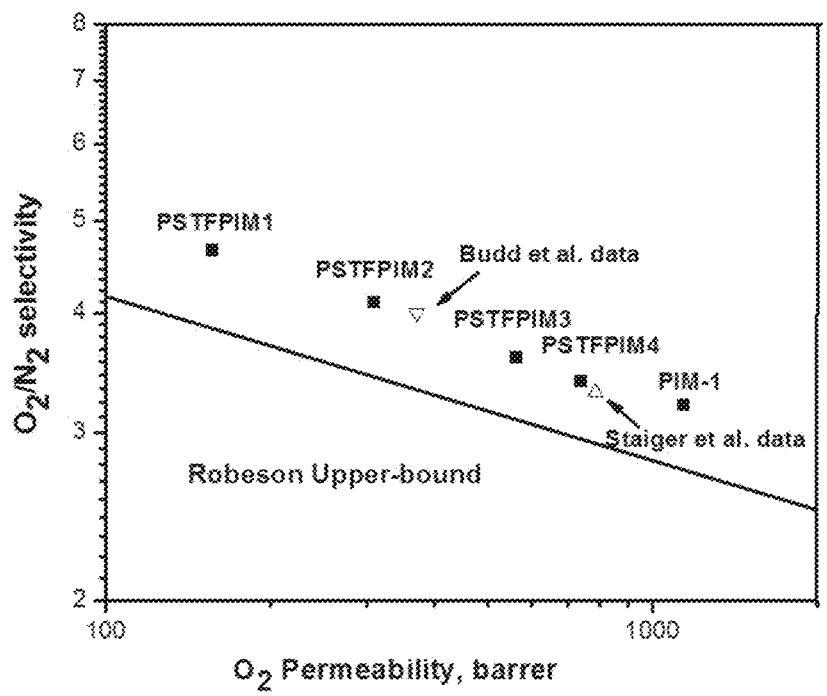
FIG. 6 depicts a graph showing the trade-off between $O_2$ permeability and $O_2/N_2$ selectivity of PIM-1 and TFMPSPIM1-4 membranes relative to the Robeson upper bound line.

Although the permeability of $O_2$ is reduced with increasing amounts of —$CF_3$ and —$SO_2C_6H_5$ groups, TFMPSPIM1-4 permeability/selectivity data points are all above the upper bound line reported by Robeson, as shown in FIG. 6. FIG. 6 illustrates the trade-off between $O_2$ permeability and $O_2/N_2$ selectivity of PIM-1, TFMPSPIM1-4 membranes relative to the Robeson upper bound line. ∇ is data from Budd et al. which are for measurements reported at 200 mbar (2.9 psia) feed pressure at 30° C. [Budd 2005b]. Δ is data from Staiger et al. which are for measurements reported at 4 atm (58.8 psia) feed pressure 35° C. [Staiger 2008].

In comparison with PIM-1, which was tested under the same conditions, TFMPSPIM1-4 have significantly higher $O_2/N_2$ and $CO_2/N_2$ selectivity. From a material and structural viewpoint, chain rigidity imparts increased selectivity but lower permeability, whereas greater interchain distance imparts higher permeability but lower selectivity. The —$CF_3$ and —$SO_2C_6H_5$ groups in TFMPSPIM1-4 are hidden within the spirocyclic main chain structure, which maintains its zig-zag conformation. While these pendant groups do not increase FFV, they increase chain stiffness and likely have an effect of inter-chain space filling. Compared to data reported by Budd et al. for films cast from tetrahydrofuran and measured at low gas feed pressure, the pure-gas oxygen permeability of PIM-1 reported for the present invention (about 1,133 Barrer) is about 3-times higher, but with a reduction in oxygen/nitrogen selectivity from 4 to 3.2 (Table 6). However, data for the present invention is more consistent with that of Staiger et al; the pure-gas permeabilities and selectivities of a PIM-1 film made from methylene chloride are similar to our data for a chloroform-solution-cast PIM-1 film. The gas permeation properties of highly rigid glassy polymers depend strongly on film formation protocols, such as casting solvent type and drying conditions [Moe 1988].

Molecular Modeling

Figure 7:
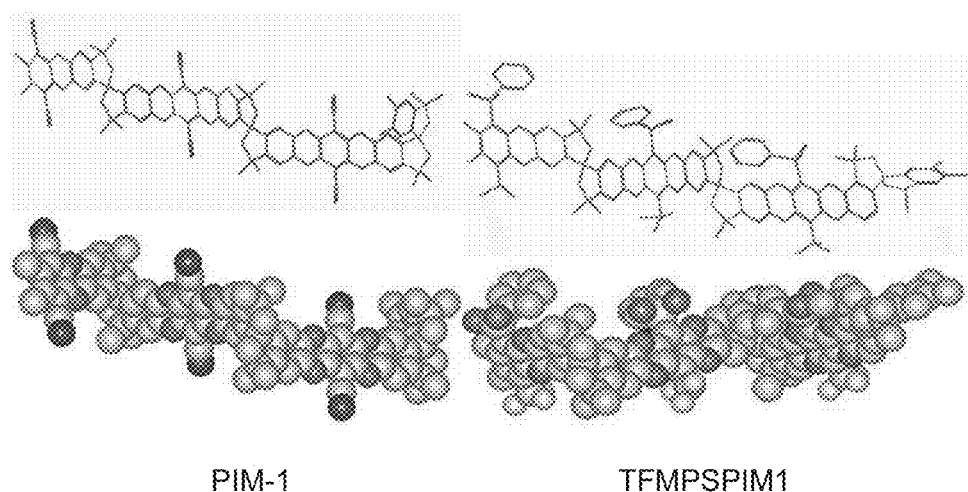
FIG. 7 depicts models of the PIM-1 and TFMPSPIM1 as calculated with energy minimization by HyperChem™ software.

Conformational analysis of TFMPSPIM1 and PIM-1 was modeled with three repeat unit lengths to study the effect and distribution of —$CF_3$ and —$SO_2C_6H_5$ on chain geometry and steric interaction. The calculation results of geometry optimization with energy minimization using the AMBER method provides a visualization of major conformational changes occurring in the polymers, as shown in FIG. 7. The chains of PIM-1 homopolymer containing —CN side groups, shown for comparison, have a relatively spiro-zigzag linear and regular ladder structure, which would lead to less chain packing. Compared with PIM-1, TFMPSPIM1 homopolymer showed a similarly unperturbed coil conformation. Although —CF$_3$ and —SO$_2$C$_6$H$_5$ are more bulky than the —CN group, they do not change the spiro-zigzag ladder chain. In addition, the rigidity of the ladder polymer chain with —CF$_3$ and —SO$_2$C$_6$H$_5$ groups can be enhanced by hindering bond distortion within the ladder chain; hence selective diffusion ability can be improved. Presumably, the pendant phenylsulfonyl group resides within the inter-chain free-volume and also acts to reduce permeability, while increasing selectivity. This is in good agreement with the gas permeation results. The molecular modeling result may help to explain why, as compared to PIM-1, the co-effects of TFMPSPIM improve their gas selectivity without overall loss of performance relative to the upper bound line.

Example 8

Preparation and Characterization of PIM Ladder Polymers Containing Tetrahydroxy Dinaphthyl (THDN) Monomer In order to investigate the effect of the spatially twisted structure in the polymer chain, this example focuses on the synthesis of CoPIMs derived from TTSBI, TFTPN and THDN. The resulting copolymers were analyzed by GPC, TGA, nitrogen sorption, and gas permeabilities were measured. Scheme 3 gives an overview of the reaction scheme to prepare THDNPIM copolymers.

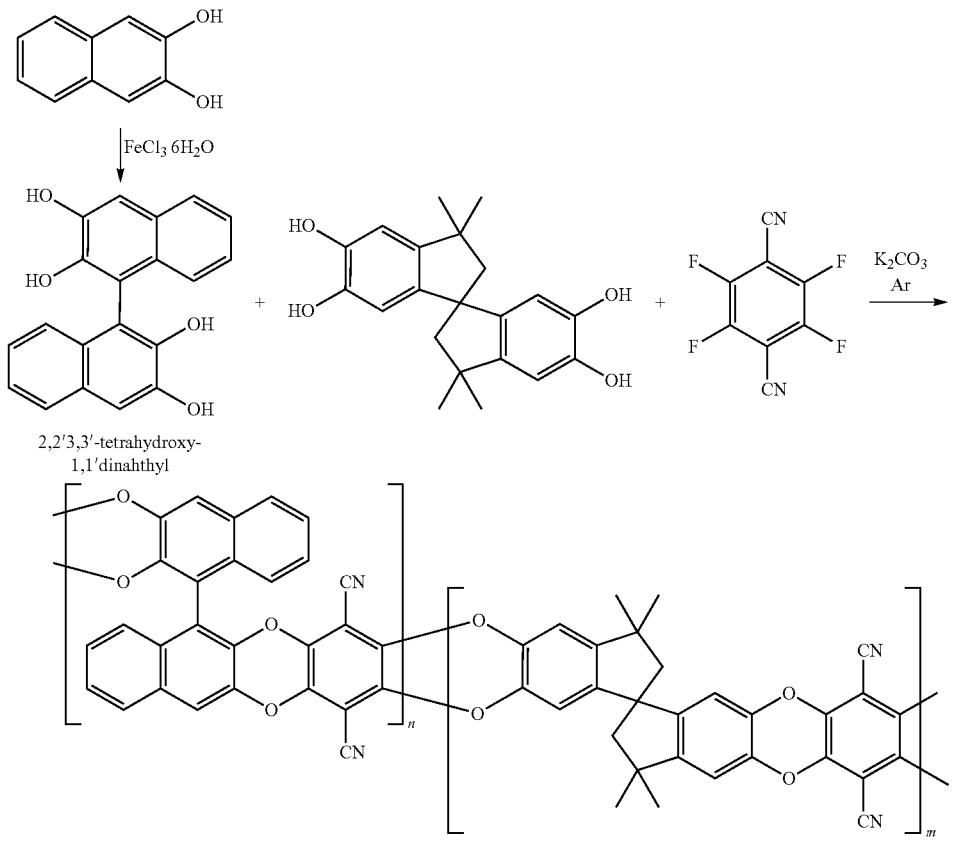

Polymerization

PIM copolymers derived from various feed ratios of TTSBI/THDN/TFTPN monomers were prepared by the aromatic nucleophilic polycondensation at 160° C. for 120 min in a manner similar to Example 5. Thus, into a 100 mL three-necked flask equipped with a magnetic stirrer, an argon inlet, and a Dean-Stark trap, with different ratio of monomers (THDN, TTSBI and TFTPN), anhydrous K$_2$CO$_3$, DMAc (monomers:DMAc=1:3.5 w:w) and toluene were added. The mixture was refluxed at 160° C. for 120 min, and then the viscous solution was poured into methanol. A yellow flexible threadlike polymer was obtained. The polymer product was dissolved in chloroform and reprecipitated from methanol. The resulting polymer was refluxed for several hours with deionized water, and dried at 100° C. for 48 h. The properties of the PIMs are summarized in Table 7.

For comparison, PIM-1 was prepared under identical reaction conditions from TTSBI and TFTPN. It should be noted that PIM-1 prepared at this temperature for shorter reaction time (40 minutes) produced high molecular weight with narrow polydispersity. Table 7 contains the approximate molecular weights and polydispersities of the copolymers, as determined by GPC against polystyrene standards. A THDNPIM homopolymer is abbreviated as THDNPIM-100 and copolymers as THDNPIM-66, THDNPIM-50 and THDNPIM-33, where 66, 50 and 33 refer to the percentage of THDN/TFTPN (molar ratio) in the polymer chain.

TABLE 7

Properties of the THDNPIM copolymer series and PIM-1

| Polymers | THDN (mol ratio) | TTSBI (mol ratio) | TFTPN (mol ratio) | $M_n$ | $M_w$ | $M_w/M_n$ |
|---|---|---|---|---|---|---|
| THDNPIM-100 | 1 | 0 | 1 | 11,000 | 24,000 | 2.2 |
| THDNPIM-66 | 2 | 1 | 3 | 13,000 | 31,000 | 2.3 |
| THDNPIM-50 | 1 | 1 | 2 | 42,000 | 77,000 | 1.8 |
| THDNPIM-33 | 1 | 2 | 3 | 116,000 | 273,000 | 2.3 |
| PIM-1 (120 min) | 0 | 1 | 1 | 58,000 | 625,000 | 10.8 |
| PIM-1 (40 min) | 0 | 1 | 1 | 55,000 | 85,000 | 1.6 |

Cyclic oligomers and cross-linking can be effectively reduced by using polycondensation reaction conditions of elevated temperature at 160° C. and high monomer concentrations. Toluene was also added to increase of solubility of tetraphenol salts and growing polymer chain. Within 40 min, the PIM-1 polymerization under optimum reaction conditions (160° C. and monomers:DMAc=1 mmol:2 mL) proceeded smoothly and no evidence of cross-linking was detected. It was observed that PIM-1 was prone to high molecular weight fractions and possible cross-linking when the reaction time exceeded 90 min under same conditions (polydispersity values up to 15), which resulted in limited $M_n$. In the absence of toluene in reaction system, crosslinking occurred rapidly, within 30 min.

Figure 8:
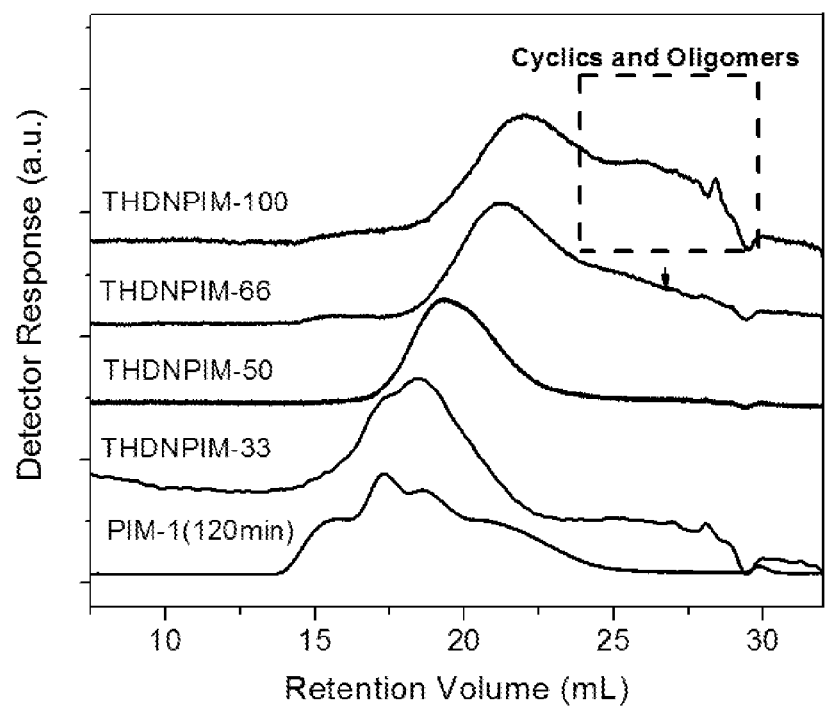
FIG. 8 depicts GPC curves for the THDNPIM polymer series and PIM-1.

As shown in FIG. 8, there are several shoulder peaks in the high molecular weight region around the main peak of PIM-1 prepared at a reaction time of 120 min, indicating high molecular weight fractions and possible cross-linking. In this example, PIM-1 was prepared under the same conditions as THDNPIM. Table 7 shows that the polydispersities of THDNPIM copolymers is in the range of 1.8-2.3, compared to over 10 for PIM-1 prepared at the extended 120 min reaction time. It is interesting to note that as the molar ratio of TTSBI in THDNPIM copolymers is increased up to THDNPIM-50, a high $M_n$ can be obtained with a low polydispersity. At higher molar ratios beyond THDNPIM-50, $M_n$ values above 10,000 could still be obtained under these conditions, with low polydispersities. In the case of THDNPIM-33, a high molecular weight and low polydispersity was obtained, with no evidence of cross-linking. Thus, under the same reaction conditions (160° C., 120 min), molecular weight broadening and cross-linking are efficiently reduced by introducing a certain ratio of THDN into the polymer chain, and high molecular weight copolymer can be obtained. A plausible explanation is that TTSBI has a higher reactivity than THDN, and its concentration was decreased by introducing THDN into the copolymerization system, resulting in less cross-linking. On another hand, although high temperature and high concentration polymerization conditions were applied in this reaction, a high molecular weight homopolymer from TFTPN and THDN still could not be obtained, most likely due to steric hindrance induced by the spatially twisted dinaphthyl center. Although the $M_n$ of THDNPIMs-100 homopolymer is higher ($M_n$=10,000 Da) than that previously reported [McKeown 2006a]($M_n$=3,000), it is still insufficient to fabricate mechanically strong films for gas permeability measurements.

Figure 9:
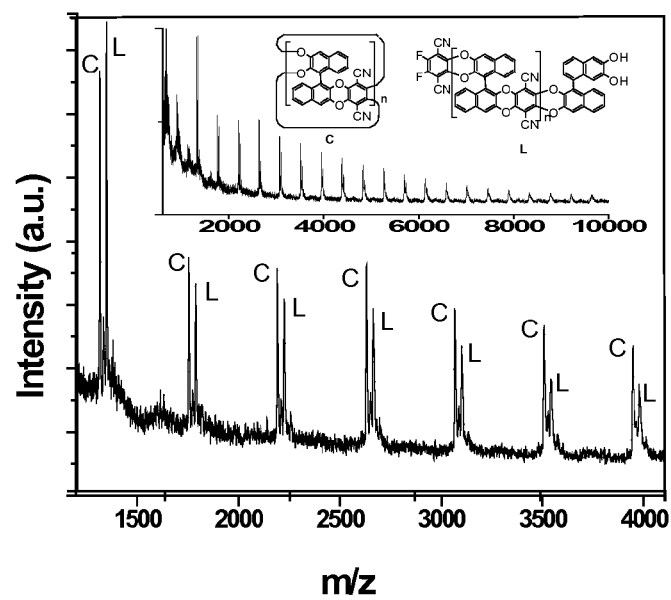
FIG. 9 depicts MALDI-TOF mass spectrum of THDN-PIM-100.

FIG. 8 shows that as the molar content of THDN monomer increases, the low molecular weight of the resulting THDN-PIM copolymers decrease. In addition, THDNPIM-100 and -66 have a significant amount of low molecular weight fractions. FIG. 9 shows that THDNPIM-100 (the homopolymer) consists mainly of cyclics and oligomers, which have two —F and two —OH groups at the polymer chain terminus.

Molecular Modeling

Figure 10:
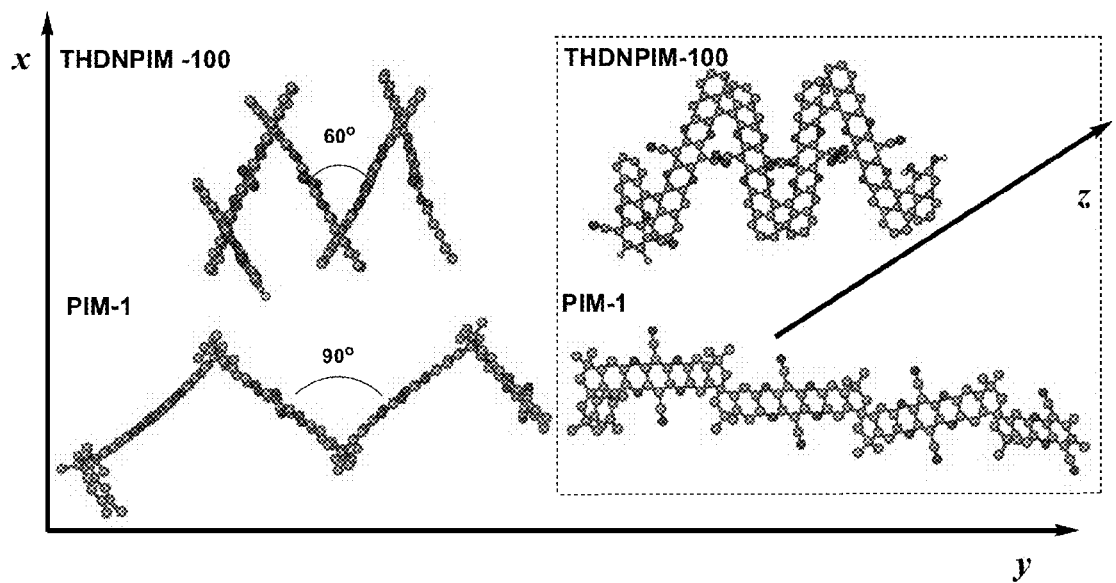
FIG. 10 depicts molecular models of PIM-1 and THDN-PIM-100 as calculated with energy minimization.

An insight as to why cyclization is favoured in chain step-growth of THDNPIM-100 was found by using the computer molecular modeling analysis. Energy minimized structural analysis of THDNPIM-100 and PIM-1 of four repeat units was performed by using HyperChem™ 7.0 software. In FIG. 10, a visual indication of major conformational changes in the polymer chain units was obtained by the calculated results of geometry optimization with minimum energy using the AMBER method. Compared to the 90° zigzag chains observed for PIM-1, the THDNPIM-100 chain has a twist angle of about 60° for each unit. The reactive end-groups are situated in a conformation conducive to form cyclic species, since the chain is more foldable and compact. With the incorporation of increasing molar ratios of TTSBI comonomer, the rigid polymer chain conformations become more irregular and randomly spiral, which reduce the chances for end-group encounters, finally preventing the formation of cyclics.

NMR Analysis

Figure 11:
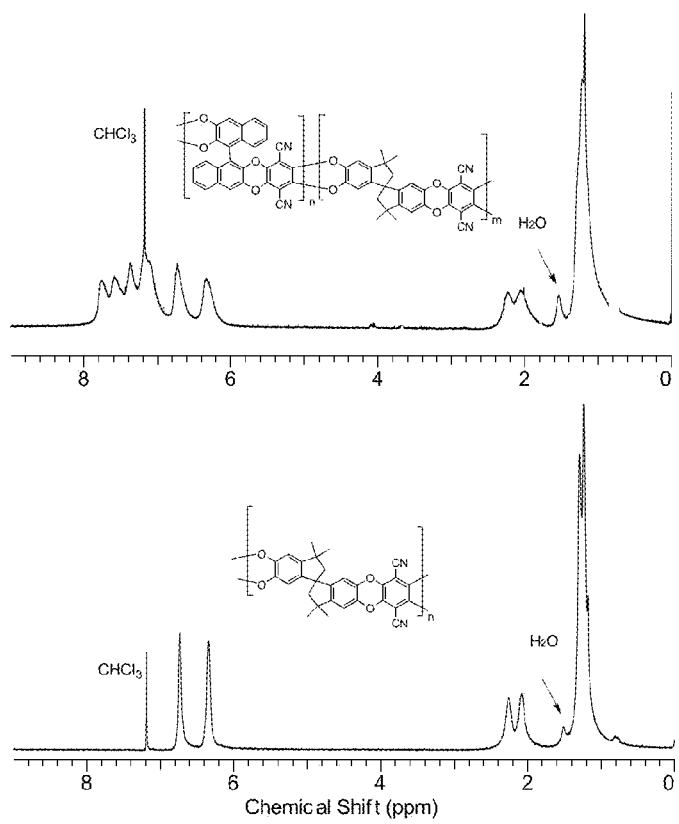
FIG. 11 depicts $^1$H NMR spectra of THDNPIM-50 and PIM-1.

All THDNPIM were fully characterized by $^1$H and $^{19}$F NMR spectroscopy. The $^1$H spectra of THDNPIM-50 (FIG. 11) were obviously similar to those of PIM-1 due to their identical TTSBI and TFTPN monomers part. The additional signals due to the THDN monomer were easily assigned in $^1$H. Furthermore, the experimental ratio of intensity values for protons on the THDN aromatic rings compared with —CH$_3$ individually is exactly 10H:12H; as expected for two repeat units of the THDNPIM-50 copolymers. Finally, the $^{19}$F NMR spectra (not shown) were collected for all three polymers. No aromatic F signal was observed.

Thermal Analysis

Thermal analyses results for the THDNPIM series and PIM-1 are compared in Table 8. All the polymers are amorphous, remaining glassy up to their decomposition temperatures (>430° C.), and have excellent thermal stabilities. No glass transitions were detected up to temperatures of 350° C. Actual onset temperatures of decomposition in nitrogen were in the range of 430-477° C. The dinaphthyl group imparts improved thermal stability, as shown by the increasing thermal stability with monomer molar ratio.

TABLE 8

Thermal properties of the THDNPIM series and PIM1

| Polymers | $T_d$ (° C.)[a] | $T_d$ (° C.)[b] | $T_{d5}$ (° C.)[c] | RW (%)[d] |
|---|---|---|---|---|
| THDNPIM-100 | 472.3 | 510.5 | 516.5 | 85 |
| THDNPIM-66 | 466.9 | 509.6 | 519.2 | 79 |
| THDNPIM-50 | 477.1 | 507.2 | 514.6 | 75 |

TABLE 8-continued

Thermal properties of the THDNPIM series and PIM1

| Polymers | $T_d$ (° C.)[a] | $T_d$ (° C.)[b] | $T_{d5}$ (° C.)[c] | RW (%)[d] |
|---|---|---|---|---|
| THDNPIM-33 | 465.9 | 504.3 | 509.5 | 73 |
| PIM-1 (120 min) | 430.1 | 492.6 | 495.4 | 68 |

[a] Actual onset temperature of decomposition
[b] Extrapolated onset temperature of decomposition measured by TGA
[c] Five percent weight loss temperature measured by TGA
[d] Residue weight at 600° C. under $N_2$ Gas Transport Properties The porosity of the polymers was probed by nitrogen sorption BET analysis at 77 K. The THDNPIM were precipitated from chloroform into methanol, followed by extensive washing with methanol prior to sorption measurements. PIM-1 was tested under the same conditions and used as a reference material. Nitrogen sorption measurements on these polymers revealed that samples were microporous. As shown in Table 9, the adsorption average pore width of THDNPIM became slightly smaller with increasing molar content of THDN, with the exception of THDNPIM-100, and BET data changed from 729 m²·g⁻¹ for PIM-1 to 560 m²·g⁻¹ through the copolymer series. The polymer chain packing can be calculated by fractional free volume (FFV), which is listed in Table 9 [Bondi 1964; Van Krevelen 1990; Chern 1987]. The calculated FFV values of THDNPIM are almost identical to PIM-1, though the density of PIM-1 is somewhat lower than those of the THDNPIM series. Since the amount of pore deformation during the adsorption process should be considered, the reason for the difference may be that the flexibility of the dinaphthyl bond is significantly higher than that of the spirobisindane bond. As the interfacial energy in a microporous system is rather high, this can result in elastic pore closure by deformation of the dinaphthyl bond during testing. THDNPIM-100 also shows good microporosity, but it consists mainly of cyclics and oligomers and is thus not suitable for comparison with the other polymers.

TABLE 9

Physical properties of THDNPIM and PIM-1

| Polymers | $\rho$, g/cm³ | $V_{sp}$, cm³/g | M, g/mol | $V_w$, cm³/mol | $V_f$, cm³/g | FFV | $S_{BET}$, m²·g⁻¹ |
|---|---|---|---|---|---|---|---|
| THDNP-100 | 1.14 | 0.88 | 438.4 | 219.4 | 0.229 | 0.26 | 311 |
| THDNP-66 | 1.12 | 0.89 | 445.8 | 228.4 | 0.224 | 0.25 | 560 |
| THDNPIM-50 | 1.11 | 0.90 | 449.4 | 232.8 | 0.227 | 0.25 | 632 |
| THDNPIM-33 | 1.09 | 0.92 | 453.1 | 237.3 | 0.239 | 0.26 | 709 |
| PIM-1 (40 min) | 1.06 | 0.94 | 460.5 | 246.3 | 0.244 | 0.26 | 729 |

In glassy or rubbery polymers, there is a trade-off relationship between gas permeability and selectivity for common gases. In general, higher permeability is gained at the cost of lower selectivity and vice versa. An upper bound performance for this trade-off relationship was proposed by Robeson [Robeson 1991]. Single gas permeability coefficients (P) were measured on polymer dense films of PIM-1 and THDNPIM-33 for $O_2$, $N_2$, He, $H_2$, $CO_2$ and a summary of these P values and ideal selectivities ($\alpha$) for various gas pairs are shown in Table 10.

TABLE 10

Gas permeabilities and ideal selectivities of THDNPIM-33 and PIM-1

| Polymers | P (Barrer[a]) | | | | | $\alpha^b$ | | | |
|---|---|---|---|---|---|---|---|---|---|
| | $O_2$ | $N_2$ | He | $H_2$ | $CO_2$ | $O_2/N_2$ | $CO_2/N_2$ | $He/N_2$ | $H_2/N_2$ |
| THDNPIM-33 | 1030 | 271 | 1138 | 2601 | 5149 | 3.8 | 19 | 4.2 | 9.6 |
| PIM-1 (120 min) | 1560 | 547 | 1531 | 3364 | 7329 | 2.85 | 13.4 | 2.8 | 6.7 |
| PIM-1 (40 min) | 1133 | 353 | 1114 | 3042 | 5366[a] | 3.2 | 15 | 3.1 | 8.6 |

Figure 13:
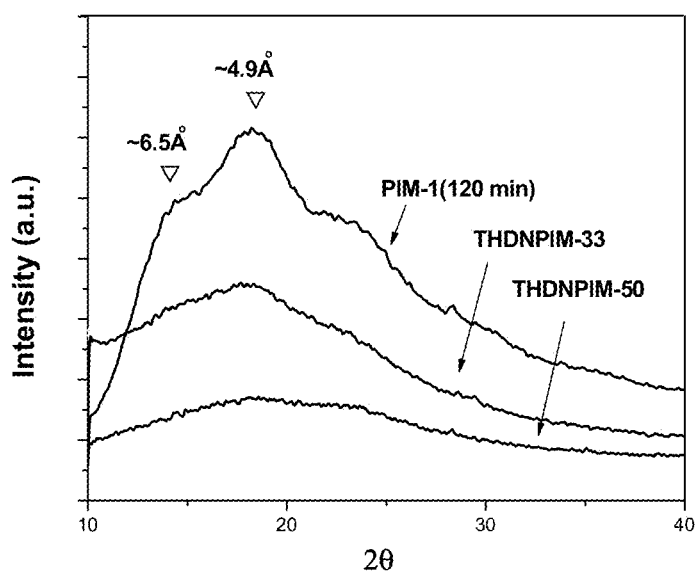
FIG. 13 depicts WAXD of THDNPIM-33, THDNPIM-50 and PIM-1.

[a] Permeability coefficients measured at 25° C. and 50 psig pressure.
1 Barrer = $10^{-10}$ [cm³(STP)·cm]/(cm²·s·cmHg)
[b] Ideal selectivity $\alpha = (P_a)/(P_b)$ THDNPIM-33 exhibited higher selectivity, coupled with some reduction in gas permeabilities, compared with PIM-1. The overall permeability/selectivity performance combines to exceed the Robeson upper bound line for $O_2/N_2$. From a material viewpoint, a shorter interchain distance imparts higher selectivity but lower permeability. In this case, THDN units shorten the distance between contorted centers, while maintaining a zig-zag structure, hence selectivity increased. Molecular modeling analysis indicates that gas permeabilities for THDNPIM-33 were not excessively reduced, even though the THDN structure is more compact and has a shorter distance between contorted centers and smaller twist angle. FIG. 10 shows that PIM-1 and THDNPIM-100 have similarly unperturbed zig-zag coil structures when viewed from 'x' and 'y' axes perspective. The angle at the spatially twisted dinaphthyl center in THDNPIM-100 (approximately 60°) is considerably smaller than that at the spirobisindane center in PIM-1 (approximately 90°). When both polymers are compared from the 'z' axis perspective, PIM-1 has an offset-linear conformation, whereas THDNPIM-100 has a zig-zag structure. This suggests that THDNPIM-100 is potentially even more contorted than PIM-1, which could result in less efficient chain packing. The addition of THDN units into copolymers would also have the same effect. This is in good agreement with the gas permeability results. Although the distance between the twisted dinaphthyl units is shorter and the kink angle is smaller than PIM-1, there was little apparent change in the interchain spacing throughout the THDNPIM copolymer series, as shown by FFV (Table 9). BET data shows that the surface area of the THDNPIM-33 copolymer is similar to PIM-1, and as the molar content of THDN increases in the copolymer, surface area decreases. Increasing the molar content of THDN also increases the amorphous nature of the copolymer, as shown by the disappearance of peaks in the X-ray diffraction measurements in FIG. 13.

Figure 12:
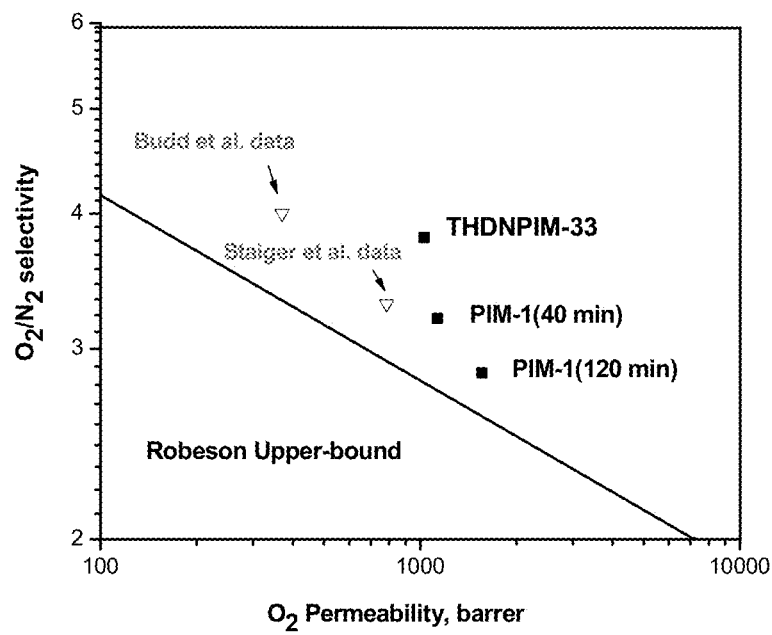
FIG. 12 depicts a graph showing the trade-off between $O_2$ permeability and $O_2/N_2$ selectivity of THDNPIM-33 and PIM-1 membranes relative to the Robeson's upper bound.

FIG. 12 shows the gas permeability/selectivity trade-off plot for the O2/N2 gas pair in relation to the Robeson upper-bound. The V symbols show previous data reported by Budd et al. and by Staiger et al., for PIM-1. The data from Budd et al. [Budd 2005b] was reported at 200 mbar (2.90 psia) feed pressure at 30° C. The data from Staiger et al. [Staiger 2008] was reported at 4 atm (58.8 psia) feed pressure 35° C. Compared to data reported by Budd et al. for films cast from tetrahydrofuran and measured at very low gas feed pressure, the oxygen permeability of chloroform-cast films of PIM-1 (reaction for 120 min, high polydispersity material) reported herein (about 1,560 Barrer) is about 4-times higher, but with a reduction in oxygen/nitrogen selectivity from 4.0 to 2.8. Also shown in FIG. 12 is comparative PIM-1 data for PIM-1 produced at a reaction time of 40 min (low polydispersity). The disparity in results arises as the gas permeation properties of highly rigid glassy polymers depend strongly on film formation protocols, such as casting solvent type and drying conditions. As shown in Table 10 and FIG. 12, the THDN-PIM-33 copolymer, had an excellent combination of properties and was significantly more selective for gases/$N_2$ than PIM-1. The selectivity coupled with high permeability combines to exceed the Robeson upper-bound line for $O_2/N_2$. The results indicate that THDM can be incorporated as a comonomer for the synthesis of high molecular weight PIMs and tune gas permeability, selectivity and other properties of PIM copolymers.

Example 9

Preparation and Characterization of PIM Ladder Polymers Containing Disulfone-Based Monomers (BSPIMs)

This example focuses on the synthesis of new PIMs derived from sulfone monomers of Example 3. The effect of the sulfone side groups on microporosity for gas permeation behavior is investigated. The new PIM copolymers were prepared from three different tetrafluoro disulfone monomers (Scheme 4), such that the resulting PIM copolymer contains bulky, rigid groups. The disulfone-based PIMs present a new class of microporous polymers, and the structures, synthesis, physical properties, including the gas separations properties of this new class of PIMs are reported in this example.

Monomer Synthesis

The synthesis of disulfone monomers comprised two steps: aromatic nucleophilic substitution reaction and oxidation. Different from the known procedures [Kulka 1959; Robson 1963; Langille 1972], the sodium thiolate and pyridine mixture was added dropwise to hexafluorobenzene at −20° C. instead of adding hexafluorobenzene into sodium thiolate and pyridine mixture at reflux temperature (above 115° C.). Hexafluorobenzene easily reacts with thiol groups under basic conditions by a aromatic nucleophilic substitution reaction, especially at an elevated temperature. Even at room temperature, the addition of more than a two molar ratio of hexafluorobenzene to sodium thiolate still resulted in the formation of 1,4-difluoroterathiobenzene compounds. According to the modified synthesis method, the side reactions were successfully avoided and three dithioether monomers were obtained in high yield. It was also found that the oxidation of thio groups was not complete by using excess $H_2O_2$ in heterogeneous acetic acid suspension at 100° C. for 1 hour. After 1 hour oxidation, only 20-30% thio groups were oxidized (observed from $^1H$ NMR spectra), which is different from the previous work [Robson 1963]. In general, the oxidation of dithio compounds is completed only after at least 24 h at 100° C. due to the poor solubility of partially oxidized compounds. TFBESB was oxidized without prior purification of the dithio compound, because the resulting disulfone monomer is more easily purified by recrystallization.

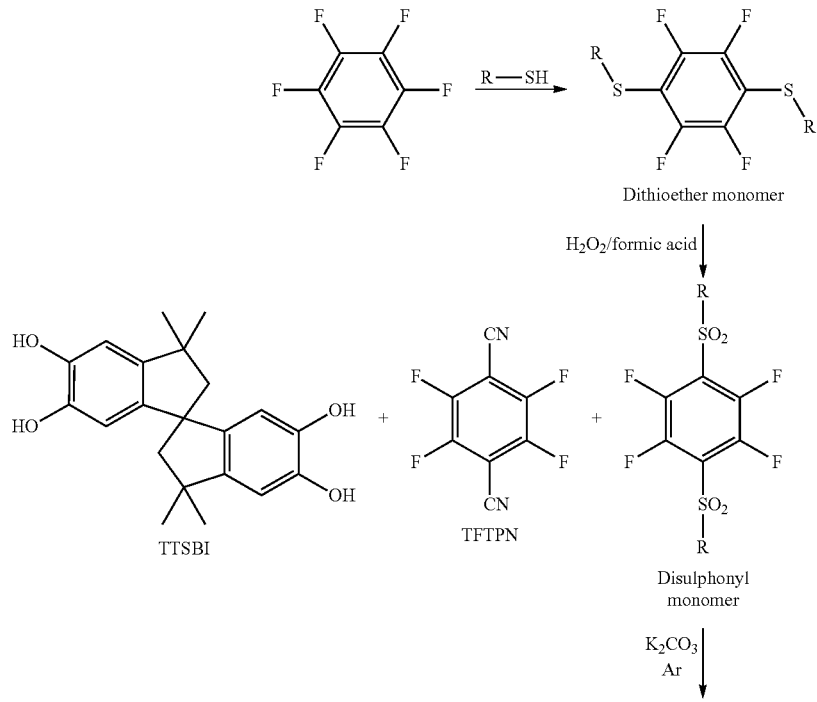

Scheme 4: Synthesis of BSPIM1-3 Series Copolymers

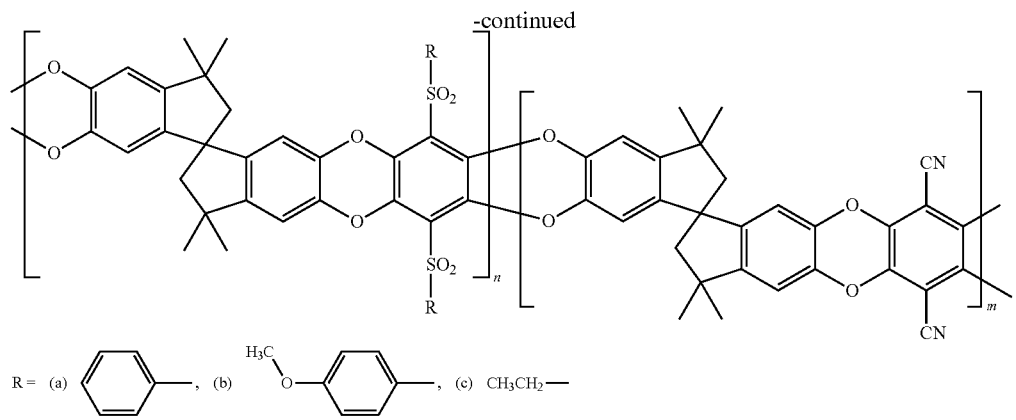

Polymerization

In general, BSPIMs-100, BSPIMs-50 and BSPIMs-33 were synthesized by copolymerization of TTSBI, TFTPN, and disulfone monomers (suffixes -100, -50, and -33 refer to disulfone to TTSBI ratio, i.e. monomer molar ratios 1:0:1; 2:1:1; 3:2:1) using a procedure similar to that of PIM-1 in Example 5.

Thus, into a 100 mL three-necked flask equipped with a magnetic stirrer, an argon inlet, and a Dean-Stark trap, TFTPN, TTSBI and disulfone monomers, anhydrous $K_2CO_3$, DMAc, and toluene were added. The mixture was refluxed at 160° C. for 40-60 min and the resulting viscous polymer solution was precipitated into methanol. A yellow flexible threadlike polymer was obtained. The polymer product was dissolved into chloroform and reprecipitated from methanol. The resulting polymer was refluxed for several hours with deionized water, and dried at 100° C. for 48 h.

Three series of ladder BSPIMs containing disulfonyl groups and —CN groups were prepared via the SNAr polycondensation described above using various feed ratios of TTSBI/TFTPN/disulfone monomers. The compositions and molecular weights of the polymers are listed in Table 11. The homopolymers are referred to as BSPIMs-100 and the copolymers are identified as BSPIMs-50, and BSPIMs-33, where PIM stands for polymer of intrinsic microporosity, BS stands for disulfonyl groups, and 50 and 33 represents the percentage of disulfone monomer/TTSBI (molar ratio) in the copolymers.

According to the polycondensation reaction mechanism for poly(arylene ether)s, high temperature and high concentration should be favorable for increasing the solubility of phenoxide salt and growing polymer chain, hence the appearance of cyclic oligomers and crosslinked structures could be effectively reduced. The polymerizations of PIM-1 and related PIM copolymer structures (TFMPSPIMs) are disclosed herein above using high monomer concentrations (>25% wt) and at elevated temperatures (e.g. 160° C.). Excess toluene is introduced into the reaction not only to remove water, but also to provide solubility enhancement of the polymer. The reactions proceed smoothly and no evidence of crosslinking occurred.

In contrast, the polycondensation of BSPIMs of this example are different from PIM-1 and TFMPSPIMs. According to the aromatic nucleophilic substitution reaction, there are two main factors influencing the substitution occurring in the aromatic system: (i) electronic activation and deactivation; and, (ii) steric deactivation. In general, it can be assumed that every substituent ortho- to the substitution site has some steric effect on the reaction rate. However, for the majority of the data reported before, the electronic effect of the electron donating or withdrawing group appears to be far more pronounced than the steric effect [Bunnett 1951]. It is well known that electron withdrawing groups have different electronic activation, in the sequence of —$SO_2R$>—$CF_3$>—CN [March 1970]. Because PIMs have a rigid ladder structure,

TABLE 11

Compositions and molecular weights of BSPIM1-3 and PIM-1

| Polymers | TTSBI (molar ratio) | Disulfone monomer (molar ratio) | TFTPN (molar ratio) | $M_n$ | $M_w$ | $M_w/M_n$ |
|---|---|---|---|---|---|---|
| BSPIM1-100 | 1 | 1 [a] | 0 | 66,000 | 413,000 | 6.2 |
| BSPIM1-50 | 2 | 1 [a] | 1 | 63,000 | 453,000 | 7.1 |
| BSPIM1-33 | 3 | 1 [a] | 2 | 43,000 | 187,000 | 4.3 |
| BSPIM2-100 | 1 | 1 [b] | 0 | 58,000 | 625,000 | 10.8 |
| BSPSM2-50 | 2 | 1 [b] | 1 | 46,000 | 350,000 | 7.6 |
| BSPIM2-33 | 3 | 1 [b] | 2 | 41,000 | 84,000 | 2.1 |
| BSPSM3-100 | 1 | 1 [c] | 0 | 49,000 | 478,000 | 9.7 |
| BSPIM3-50 | 2 | 1 [c] | 1 | 52,000 | 421,000 | 8.1 |
| BSPIM3-33 | 3 | 1 [c] | 2 | 95,000 | 489,000 | 5.1 |
| PIM-1 | 1 | 0 | 1 | 58,000 | 193,000 | 3.3 |

Figure 14:
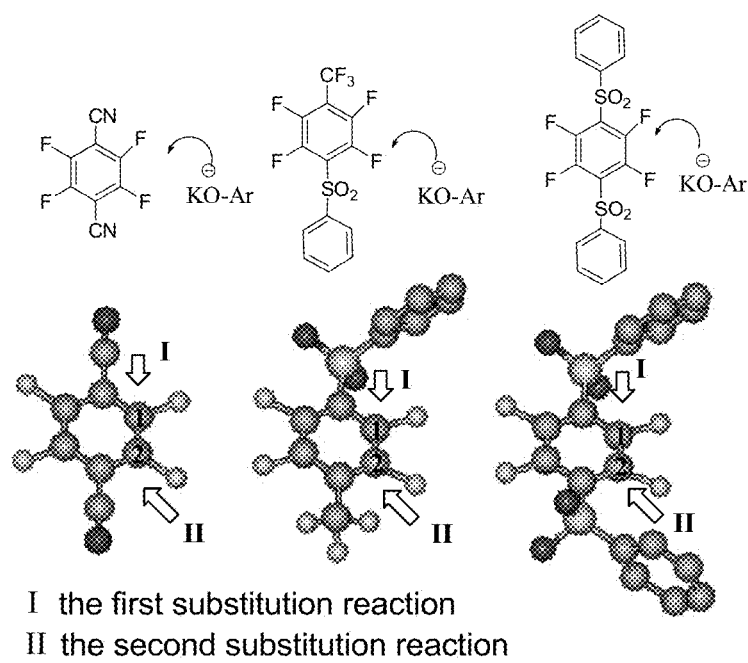
FIG. 14 depicts aromatic nucleophilic substitution reaction of tetrafluoro monomers.

[a] monomer (a) in Scheme 4
[b] monomer (b) in Scheme 4
[c] monomer (c) in Scheme 4 which is different from linear flexible polymers, the steric deactivation effect may become important. In the first substitution reaction (I) shown in FIG. 14, wherein a phenoxide nucleophile displaces a fluorine atom, the steric effect may not be obvious because the electrophile can attack perpendicular to the ring. Comparing three tetrafluoro-monomers, the initial substitution reactions will occur at the ortho-activated fluorine atom (atom 1) near —$SO_2R$ or —CN groups. When the second substitution reaction (II) forms the dibenzodioxane-based structure, the Ar—O—$K^+$ must attack the fluorine atom (atom 2) on the same side, from the horizontal direction, resulting in a quasi-planar dioxane ring. Therefore, the steric effects may become significant for dioxane ring formation in PIMs. If the electron withdrawing groups are not too sterically bulky, such as —CN and —$CF_3$, the dibenzodioxane ring structure will be formed relatively easily. On the other hand, —$SO_2R$ is large enough to prevent electrophilic attack efficiently from the horizontal direction. Hence, under the high concentration reaction conditions used, after substitution reaction (I) occurs, there may be a competing substitution reaction (I) (perpendicular direction) on atom 1 of another monomer rather than the desired dibenzodioxane ring formation brought about by substitution reaction (II) (horizontal direction) on atom 2 of the same monomer. However, if reaction conditions are used whereby the concentration of disulfone monomer is low, dibenzodioxane ring formation is more likely to occur after the initial substitution reaction (I) due to the dilution effect. Meanwhile the reactivity of comonomer TFTPN is not as high as the disulfone-based monomers. Hence, with a progressively decreasing molar ratio of disulfone-based monomer to TTSBI, polydispersity is reduced, as observed by GPC. The GPC curves of BSPIMs-100 (not shown) reveal several shoulder peaks in the high molecular weight region along with the main peak. A minor gel fraction indicated that some crosslinking had occurred during the reaction. With decreasing ratios of disulfone-based monomers, only negligible gel formation was observed. The $M_n$ of all three BSPIMs-33 copolymers (Table 11) are above 41,000 Da and the polydispersity indices are in the range of 2-5. Although the polydispersity indices of BSPIMs-33 are somewhat higher than typical PIM-1 and PSTFPIM obtained under the same conditions, the quality of the copolymers is still high enough to provide solution-cast robust free-standing films for gas permeability measurements.

NMR Analysis

Figure 15:
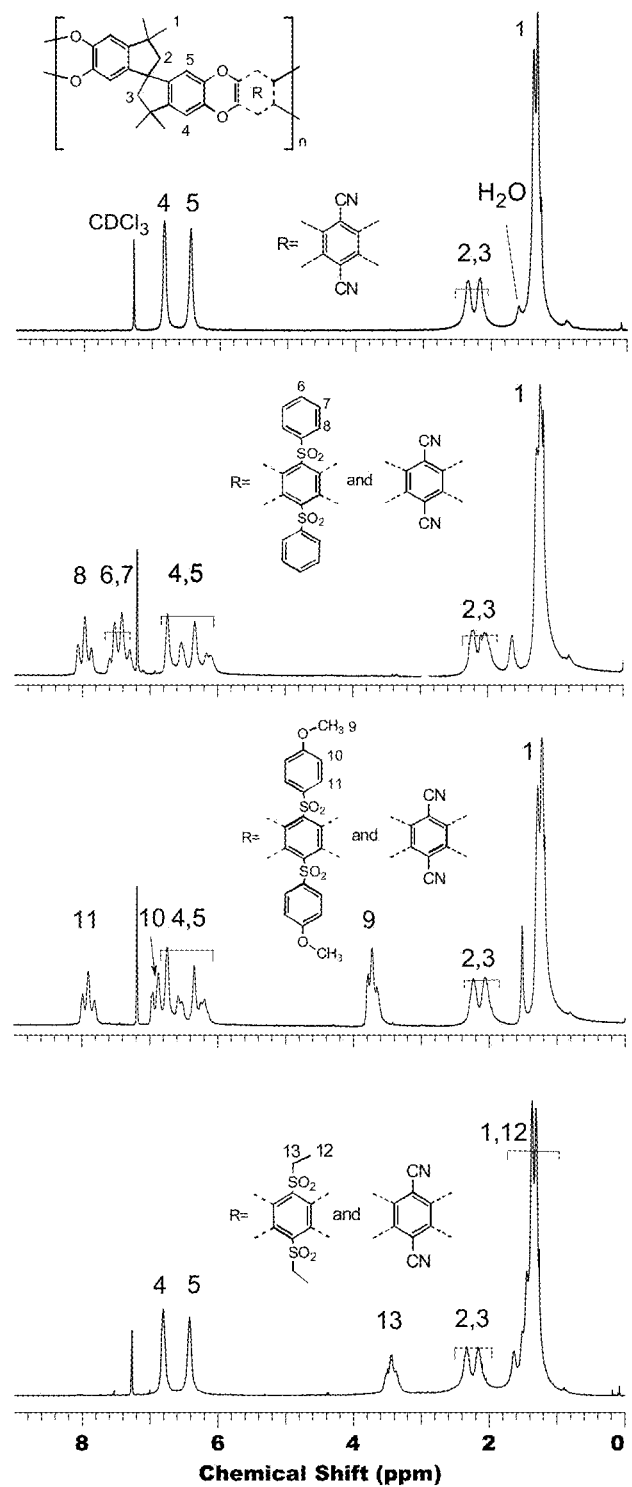
FIG. 15 depicts $^1$H NMR spectra of PIM-1 (top), BSPIM1-50, BSPIM2-50 and BSPIM3-50.

All three BSPIMs-50 were fully characterized by $^1H$ and $^{19}F$ NMR spectroscopy. The $^1H$ spectra of BSPIMs-50 were obviously similar to those of PIM-1 due to their identical TTSBI and TFTPN monomer content. The additional signals due to the different disulfone monomer were easily assigned in $^1H$ NMR. Furthermore, the experimental ratio of intensity values for aromatic protons H-8, 11 or 13 compared with aliphatic protons H-2,3 was found to be exactly as expected; for example, the spectra of the BSPIM-50 displayed in FIG. 15 all had proton ratios of exactly 4H:8H per repeat unit.

A three-dimensional representation of the PIM polymer structures explains better what is observed in $^1H$ NMR spectroscopy. In 3-D it is clear that one of the methyl groups is within very close proximity of H-5 and therefore the electron cloud of the $CH_3$ group is shielding this proton, hence its very low chemical shift (6.4 ppm) for an aromatic proton. From the H-4 perspective, the two methyl groups are more distant, hence no shielding and the higher chemical shift (6.8 ppm) is observed. This combines to explain why the methyl groups (H-1) do not appear as a singlet but as two singlets, because they are not equivalent in a 3-D representation. The same principle also applies to H-2 and H-3.

Those same H-4 and H-5 protons appear at the same position for both PIM-1 and BSPIM3-50 because the pendant groups, —CN and —$SO_2CH_2CH_3$ respectively, are small and sufficiently distant from the aromatic protons that they have no effect on them. On the other hand, the two PIM polymers BSPIM1-50 and BSPIM2-50 have bulky pendant phenyl groups with aromatic annular effects (ring current). These groups will cause H-4 and H-5 to appear at different chemical shifts. Hence, multiple H-4 and H-5 signals appear for BSPIM1-50 and BSPIM2-50 but not for PIM-1 and BSPIM3-50.

The $^{19}F$ NMR spectra (not shown) were collected for all BSPIMs homo- and copolymers. No aromatic F signal was observed.

Thermal Analysis

Thermal analyses for BSPIMs and PIM-1 were carried out and the results are summarized in Table 12. All polymers are amorphous and have no discernable $T_g$ up to their decomposition temperatures (>317° C.). TGA experiments showed that all polymers had excellent thermal stabilities and the actual onset temperature of decomposition in nitrogen ranged from 317-407° C. There was also some trend between the decomposition temperature and the monomer ratio. Generally, polymers with —$SO_2Ar$ groups have high thermal stability. However, the —CN side group can enhance the thermal properties due to strong dipolar interactions. With increasing the molar ratios of —CN groups in the BSPIMs, the onset of thermal decomposition also increased, as shown in Table 12. However, BSPIM homopolymers and copolymers all showed very good thermal stability even after the replacement of —CN with —$SO_2R$ groups.

TABLE 12

Thermal properties of the BSPIM1-3 series and PIM-1

| Polymers | $T_d$ (° C.)$^a$ | $T_d$ (° C.)$^b$ | $T_{d5}$ (° C.)$^c$ | RW (%)$^d$ |
|---|---|---|---|---|
| BSPIM1-100 | 346.5 | 421.2 | 421.5 | 53.5 |
| BSPIM1-50 | 372.3 | 451.91 | 449.84 | 63.0 |
| BSPIM1-33 | 407.7 | 475.2 | 484.67 | 63.7 |
| BSPIM2-100 | 329.7 | 417.2 | 412.5 | 51.0 |
| BSPIM2-50 | 361.8 | 447.29 | 447.65 | 59.0 |
| BSPIM2-33 | 384.7 | 464.9 | 475.92 | 62.5 |
| BSPIM3-100 | 304.0 | 357.1 | 357.9 | 40.0 |
| BSPIM3-50 | 317.0 | 398.46 | 376.33 | 48.0 |
| BSPIM3-33 | 362.9 | 423.9 | 434.92 | 61.5 |
| PIM-1 | 429.6 | 492.6 | 495.4 | 68.0 |

Figure 16:
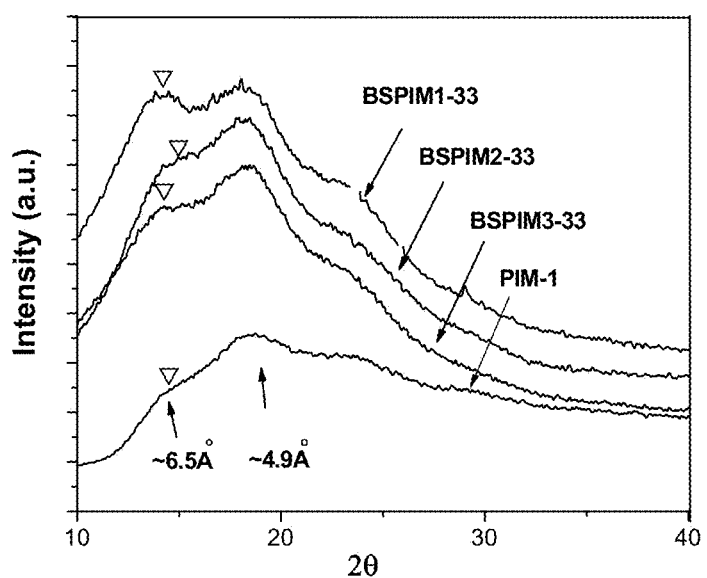
FIG. 16 depicts WAXD of BSPIMs-100 and PIM-1.

$^a$Actual onset temperature of decomposition
$^b$Extrapolated onset temperature of decomposition measured by TGA
$^c$Five percent weight loss temperature measured by TGA
$^d$Residue weight at 600° C. under $N_2$ X-Ray Diffraction Studies WAXD revealed that BSPIMs-100 were amorphous polymers. Two main broad peaks were observed for all polymers (FIG. 16). According to Bragg's Law, the peak representing 4.9 Å might be attributed to chain-to-chain distance of space-efficiently packed chains. On the other hand, the second peak found at a d-spacing of approx. 6.5 Å corresponds to more loosely packed polymer chains [Weber 2007]. As shown in FIG. 16, the d-spacing is 5.9 Å for BSPIM2 and 6.5 Å for PIM-1. It becomes larger with decreasing size of disulfonyl groups in the main chain, suggesting that different disulfonyl groups affect polymer chain packing. The increasing size of disulfonyl groups leads to lower FFV due to inter-chain space filling.

Free Volume Analysis

The fractional free volume (FFV) is calculated using the following equations:

$$FFV = (V - V_0)/V \text{ and } V = M/\rho \text{ and } V_0 = 1.3 V_w$$

where V is the total molar volume of the monomer unit (cm³/mol), M is the molar mass (g/mol) of the monomer unit and ρ is the density of the film (g/cm³), which is determined experimentally (determined by measurements of the weight in air and in the ethanol). $V_0$ is the volume occupied by the chains (cm³/mol). $V_0$ is assumed to be impermeable for diffusing gas molecules. $V_w$ is the Van der Waals volume calculated using the group contribution method of Bondi [Bondi 1964, Van Krevelen 1990; Lee 1980]. According to Bondi, a good approximation of relation between $V_0$ and $V_w$ is given by the last equation and the results are given in Table 13. The FFV varied from a minimum of 0.09 for BSPIM2-100 to a maximum of 0.26 for PIM-1. The FFV of BSPIMs-33 is around 0.20. Compared to PIM-1, BSPIMs-33 pack more efficiently.

TABLE 13

Physical properties of BSPIM1-3 series and PIM-1

| Polymers | ρ, g/cm³ | V, cm³/g | M, g/mol | $V_w$, cm³/mol | $V - V_0$, cm³/g | FFV |
|---|---|---|---|---|---|---|
| BSPIM1-100 | 1.356 | 0.737 | 690.78 | 349.2 | 0.080 | 0.11 |
| BSPIM1-50 | 1.207 | 0.829 | 575.63 | 297.8 | 0.156 | 0.19 |
| BSPIM1-33 | 1.187 | 0.842 | 537.25 | 280.6 | 0.163 | 0.19 |
| BSPIM2-100 | 1.369 | 0.730 | 750.83 | 382.4 | 0.068 | 0.09 |
| BSPIM2-50 | 1.234 | 0.810 | 605.66 | 314.4 | 0.135 | 0.17 |
| BSPIM2-33 | 1.198 | 0.835 | 557.26 | 291.7 | 0.155 | 0.19 |
| BSPIM3-100 | 1.325 | 0.755 | 594.70 | 305.3 | 0.088 | 0.12 |
| BSPIM3-50 | 1.214 | 0.824 | 527.59 | 275.8 | 0.144 | 0.18 |
| BSPIM3-33 | 1.162 | 0.861 | 505.22 | 266.0 | 0.177 | 0.21 |
| PIM-1 | 1.063 | 0.94 | 460.48 | 246.3 | 0.244 | 0.26 |

Pure-Gas Permeation Properties

Single-gas permeability coefficients (P) for $O_2$, $N_2$, $CO_2$ were determined at 25° C. for dense polymer films (PIM-1, BSPIMs-33) and a summary of these P values and ideal selectivities for various gas pairs are shown in Table 14.

TABLE 14

Gas permeabilities and selectivities of BSPIM1-33, BSPIM2-33, BSPIM3-33 and PIM-1

| Polymers | P (Barrer[a]) | | | α[b] | |
|---|---|---|---|---|---|
| | $O_2$ | $N_2$ | $CO_2$ | $O_2/N_2$ | $CO_2/N_2$ |
| BSPIM1-33 | 322 | 88 | 1408 | 3.7 | 16 |
| BSPIM2-33 | 216 | 52 | 1077 | 4.2 | 20.7 |
| BSPIM3-33 | 369 | 93 | 2154 | 3.9 | 23 |
| PIM-1 | 1133 | 353 | 5366 | 3.2 | 15.2 |

[a] Permeability coefficients measured at 25° C. and 50 psig pressure 1 Barrer = $10^{-10}$ [cm³ (STP) · cm]/(cm² · s · cmHg)
[b] Ideal selectivity α = (Pa)/(Pb)

In comparison with PIM-1, the newly synthesized BSPIMs-33 exhibited higher selectivity, coupled with reductions in gas permeabilities. The selectivities for $O_2/N_2$ and $CO_2/N_2$ were in the range of 3.7-4.2 and 16-23, respectively.

These results agree with the general tendency for gas permeation through polymer membranes, i.e. higher $O_2$ and $CO_2$ permeability is gained at the cost of lower selectivity and vice versa. Robeson proposed upper bound performance lines for this trade-off relationship between permeability and selectivity [Robeson 1991]. It is especially noteworthy that the $O_2$ permeation data of BSPIMs-33 were all positioned above Robeson's upper bound line. The high permeability and selectivity of $O_2$ and $CO_2$ of the BSPIMs-33 polymers can be ascribed to the presence of both nitrile groups, which are sufficiently polar, and disulfone groups, which are bulky. While these pendant groups do not increase the FFV or reduce chain packing, they increase chain stiffness and likely have an effect of inter-chain space filling, which results in an increase in selectivity. On the other hand, the permeability decreases by enlarging the size of pendant groups on PIMs. The three disulfone groups have different effects on space filling and interchain packing. The permeability and selectivity of PIMs can be tuned by the size of pendant groups. For example, BSPIM3-33 has the best combination of permeability coupled with selectivity for $O_2/N_2$ and $CO_2/N_2$ among the three BSPIMs-33.

Molecular Modeling

Figure 17:
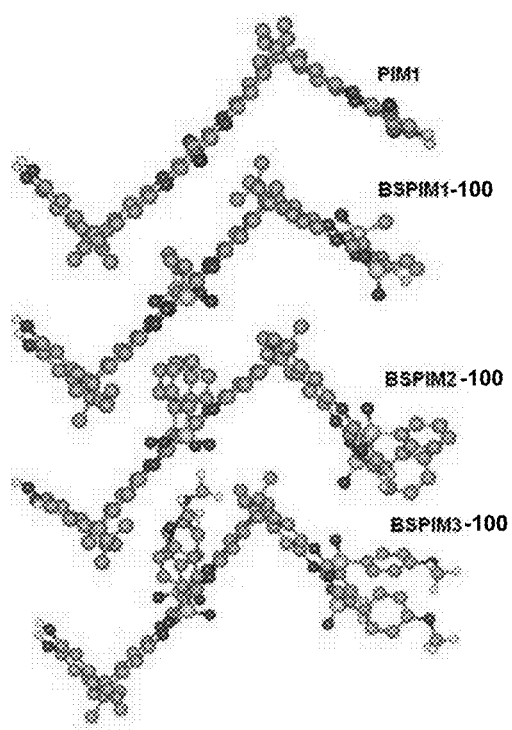
FIG. 17 depicts molecular models of the PIM-1 and BSPIMs-100 as calculated with energy minimization.

Molecular modeling analyses of BSPIMs-100 and PIM-1 with two repeat unit lengths were performed by using HyperChem™ 7.0 software for studying the effect on geometry and steric interaction of disulfonyl groups on the polymer chains. In FIG. 17, a visual indication of major conformational changes in the polymers was obtained by the calculation results of geometry optimization with energy minimization using the AMBER method. The chains of PIM-1 with —CN pendant groups shown for comparison are relatively spiro-zigzag linear and regular ladder structure, which would lead to less chain packing. Compared with PIM-1, BSPIMs showed a similarly unperturbed coil conformation. Although disulfonyl groups are more bulky than the —CN group, they do not change the overall spiro-zigzag ladder chain structure and also do not take more intermolecular space. In addition the rigidity of the ladder polymers chain with disulfonyl groups can be enhanced by hindering bond distortions within the ladder chain, hence selective diffusion ability can be enhanced. The different pendant groups also act as the interchain space fillers with different size, which results in a decrease in permeability. The molecular modeling is in agreement with the gas permeability and selectivity data and help to explain the observed gas selectivity of BSPIMs-33 versus PIM-1.

Example 10

Preparation and Characterization of PIM Ladder Polymers Containing 2,3,7,8-Tetrafluoro-5,5',10,10'-Tetraoxidethianthrene Monomers (TOTPIMs)

This example focuses on the synthesis of new PIMs derived from the 2,3,7,8-tetrafluoro-5,5',10,10'-tetraoxidethianthrene (TFTOT) monomer of Example 4. New PIM copolymers (designated TOTPIMs) were prepared from the monomer in accordance with Scheme 5.

Scheme 5: Synthesis of TOTPIM Series Copolymers

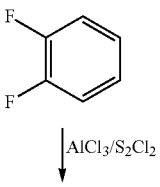

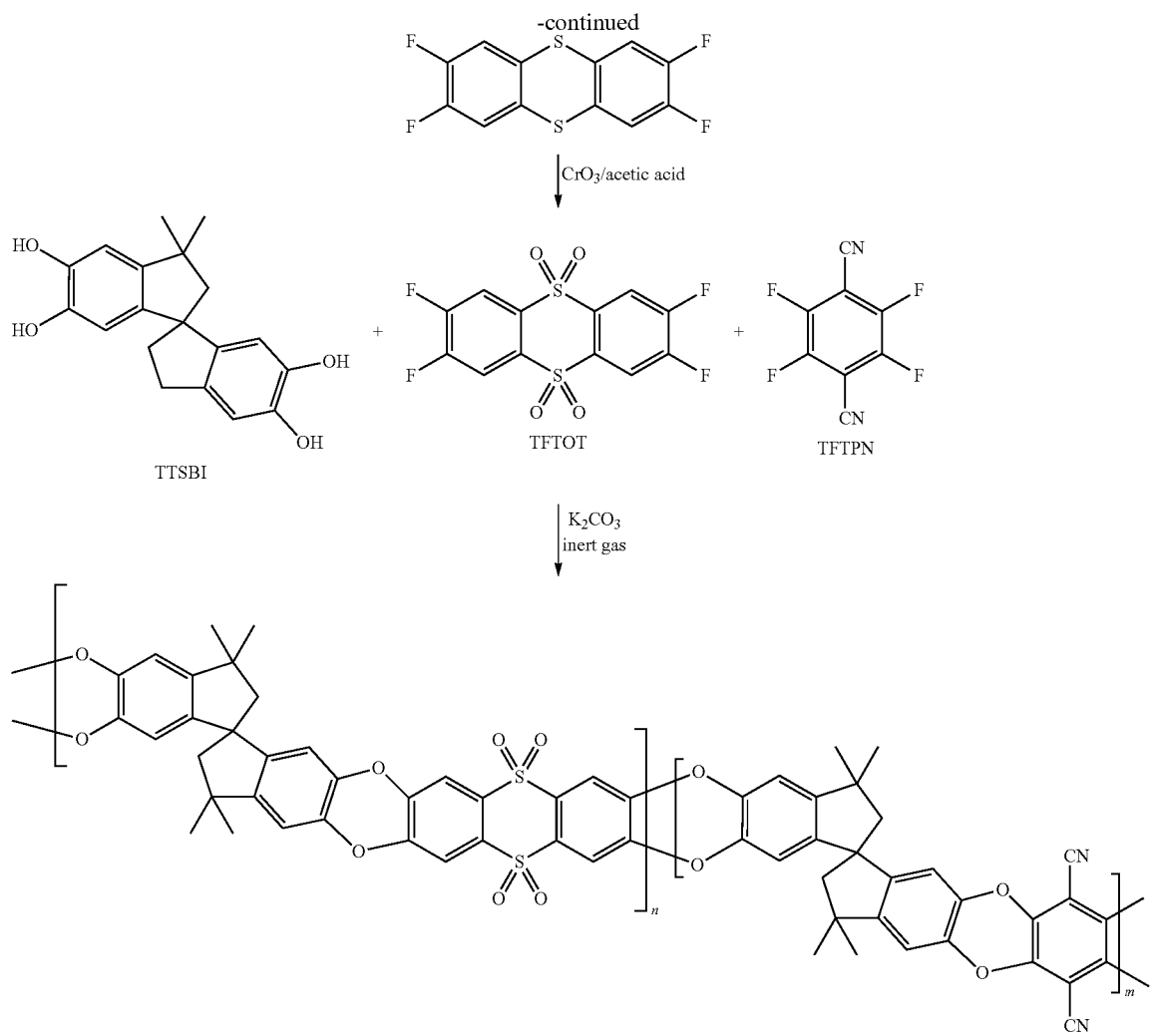

Monomer Synthesis

The 2,3,7,8-tetrafluoro-5,5',10,10'-tetraoxidethianthrene (TFTOT) monomer is a novel compound. It is somewhat analogous to 2,3,7,8-tetrachloro-5,5',10,10'-tetraoxidethianthrene listed by McKeown [McKeown 2006a] but McKeown did not report any polymers made from the tetrachloro analogue. TFTOT has superior reactivity than the tetrachloro analogue, the tetrachloro analogue being a poor choice for polycondensation reactions.

Polymerization

In general, TOTPIMs were synthesized by copolymerization of TTSBI, TFTOT and TFTPN (suffixes -100, -66, -50, -33, -25 and -20 refer to TTSBI:TFTOT:TFTPN ratio, i.e. monomer molar ratios 1:1:0, 3:2:1, 2:1:1, 3:1:2, 4:1:3 and 5:1:4, respectively) using a procedure similar to that of PIM-1 in Example 5 and as illustrated in Scheme 5. The homopolymer of TTSBI with TFTOT represented by TOTPIM-100 was not successfully isolated due to poor solubility of the polymer.

Thus, into a 100 mL three-necked flask equipped with a magnetic stirrer, an inert gas inlet, and a Dean-Stark trap, TFTPN, TTSBI and TFTOT monomers, anhydrous $K_2CO_3$, DMAc and toluene were added. The mixture was refluxed at 160° C. for 40-60 min, and the resulting viscous polymer solution was precipitated into methanol. A yellow flexible threadlike polymer was obtained in most cases. The polymer product was dissolved into chloroform and reprecipitated from methanol. The resulting polymer was refluxed for several hours with deionized water, and dried at 100° C. for 48 h. Molecular weights and monomer ratios are provided in Table 15.

TABLE 15

Compositions and molecular weights of TOTPIMs

| Polymers | TTSBI (molar ratio) | TFTOT (molar ratio) | TFTPN (molar ratio) | $M_n$ | $M_w$ | $M_w/M_n$ |
|---|---|---|---|---|---|---|
| TOTPIM-100 | 1 | 1 | 0 | — | — | — |
| TOTPIM-66 | 3 | 2 | 1 | 15,200 | 32,000 | 2.1 |

TABLE 15-continued

Compositions and molecular weights of TOTPIMs

| Polymers | TTSBI (molar ratio) | TFTOT (molar ratio) | TFTPN (molar ratio) | $M_n$ | $M_w$ | $M_w/M_n$ |
|---|---|---|---|---|---|---|
| TOTPIM-50 | 2 | 1 | 1 | 41,000 | 89,000 | 2.2 |
| TOTPIM-33 | 3 | 1 | 2 | 30,000 | 70,000 | 2.3 |
| TOTPIM-25 | 4 | 1 | 3 | 42,000 | 84,000 | 2.0 |
| TOTPIM-20 | 5 | 1 | 4 | 40,000 | 81,000 | 2.1 |

REFERENCES

The contents of the entirety of each of which are incorporated by this reference.

Alsop D J, Burdon J, Tatlow J C. (1962) *J. Chem Soc.* 1801-1805.
Aoki T. (1999) *Prog. Polym. Sci.* 24, 951-993.
Banerjee S, Maier G, Burger M. (1999) *Macromolecules.* 32, 4279-4289.
Bock H, Stein U, Rittmeyer P. (1982) *Angew Chem.* 94, 540-541.
Bondi A. (1964) *J. Phys. Chem.* 68, 441-451.
Budd, P M, Ghanem B, Msayib K, McKeown N B, Tattershall C J. (2003) *Mater. Chem.* 13, 2721-2726.
Budd P M, Ghanem B S, Makhseed S, McKeown N B, Msayeb K J, Tattershall C E. (2004a) *Chem. Commun.* 230-231.
Budd P M, Elabas E S, Ghanem B S, Makhseed S, McKeown N B, Msayeb K J, Tattershall C E, Wong D. (2004b) *Adv. Mater.* 16, 456-459.
Budd P M, McKeown N B, Fritsch D J. (2005a) *Mater. Chem.* 15, 1977-1986.
Budd P M, Msayeb K J, Tattershall C E, Reynolds K J, McKeown N B, Fritsch D. (2005b) *J. Membr. Sci.* 251, 263-269.
Budd P M, Butler A, Selbie J, Mahmood K, McKeown N B, Ghanem B, Msayib K, Book D, Walton A. (2007) *Phys. Chem. Chem. Phys.* 9, 1802-1808.
Bunnett J F, Zahler R E. (1951) *Chem. Rev.* 49, 273-412.
Carta M, Msayib K J, Budd P M, McKeown N B. (2008) *Org. Lett.* 10, 2641-2643.
Chern R T, Sheu F R, Jia L, Stannett V T, Hopfenberg H B. (1987) *J. Membr. Sci.* 35, 103-115.
Dai Y, Guiver M D, Robertson G P, Kang Y S, Lee☐ K J, Jho J Y. (2004) *Macromolecules.* 37, 1403-1410.
Dai Y, Guiver M D, Robertson G P, Kang Y S. (2005) *Macromolecules.* 38, 9670-9678.
Davankov V A, Tsyurupa M P. (1990) *React. Polym.* 13, 27-42.
Du N, Song J, Robertson G P, Pinnau I, Guiver M D, (2008) *Macromol. Rapid Commun.* 29, 783.
George S C, Thomas S. (2001) *Prog. Polym. Sci.* 26, 985-1017.
Ghanem B, McKeown N B, Harris K D M, Pan Z, Budd P M, Butler A, Selbie J, Book D, Walton A. (2007) *Chem. Commun.* 67-69.
Ghanem B, McKeown N B, Budd P M, Fritsch D. (2008) *Macromolecules.* 41, 1640-1646.
Kim T H, Koros W J, Husk G R, O'Brien K C. (1988) *J. Membr. Sci.* 37, 45-62.
Kricheldorf H R, Lomadze N, Fritsch D, Schwarz G. (2006) *J. Polym. Sci., Part A: Polym. Chem.* 44, 5344.
Kricheldorf H R, Fritsch D, Vakhtangishvili L, Lomadze N, Schwarz G. (2006) *Macromolecules.* 39, 4990-4998.
Kulka M J. (1959) *Org. Chem.* 24, 235-237.
Langille K R, Peach M E. (1972) *J. Fluorine Chem.* 407-414.
Lee W M. (1980) *Polym. Eng. Sci.* 20, 65-79.
Lee C L, Chapman H L, Cifuentes M E, Lee K M, Merrill L D, Ulman K L, Venkataraman K J. (1988) *Membr. Sci.* 38, 55-70.
Maffei A V, Budd P M, McKeown N B. (2006) *Langmuir* 22, 4225-4229.
Maier G. (1998) *Angew. Chem. Int. Ed.* 37, 2960-2974.
March J. (1970) *Advanced Organic Chemistry.* New York: McGraw-Hill, p 253.
Masuda T, Isobe E, Higashimura T, Takada K. (1983) *J. Am. Chem. Soc.* 105, 7473-7474.
McKeown N B, Hanif S, Msayib K, Tattershall C E, Budd P M. (2002) *Chem. Commun.* 2782-2783.
McKeown N B, Budd P M, Msayeb K J, Ghanem B S, Kingston H J, Tattershall C E, Makhseed S, Reynolds K J, Fritsch D. (2005) *Chem. Eur. J.* 11, 2610-2620.
McKeown N B, Budd P M, Msayib K, Ghanem B. (2006a) United States Patent Publication US 2006-0246273 published Nov. 2, 2006.
McKeown N B, Gahnem B, Msayib K J. Budd P M, Tattershall C E, Mahmood K, Tan S, Book D, Langmi H W, Walton A. (2006b) *Angew. Chem. Int. Ed.* 45, 1804-1807.
McKeown N B, Budd P M. (2006c) *Chem. Soc. Rev.* 35, 675-683.
McKeown N B, Budd P M, Book D. (2007) *Macromol. Rapid Commun.* 28, 995-1002.
Miyatake K, Hill A R, Hay A S. (2001) *Macromolecules.* 34, 4288N.
Moe M B, Koros W J, Hoehn H H, Husk G R. (1988) *J. Appl. Polym. Sci.* 36 1833-1846.
Nagai K, Masuda T, Nakagawa T, Freeman B D, Pinnau I. (2001) *Prog. Polym. Sci.* 26, 721-798.
Pandey P, Chauhan R S. (2001) *Prog. Polym. Sci.* 26, 853-893.
Paul D R, Yampolski Y. (1994) In *Polymeric gas separation membranes.* CRC Press: London, p 107.
Robeson L M. (1991) *J. Membr. Sci.* 62, 165-185.
Robeson L M, Burgoyne W F, Langsam M, Savoca A C, Tien C F. (1994) *Polymer.* 35, 4970-4978.
Robson P, Smith T A, Stephens R, Tatlow J C. (1963) *J Chem. Soc.* 7, 3692-3703.
Shibuya N, Porter R S. (1992) *Macromolecules.* 25, 6495.
Staiger C L, Pas S J, Hill A J, Cornelius C. (2008) *J. Chem. Mater.* 20, 2606-2608.
Stern S A. (1994) *J. Membr. Sci.* 94, 1-65.
Tanaka K, Okano M, Toshino H, Kita H, Okamoto K I. (1992) *J. Polym. Sci., Polym. Phys.* 30, 907-914.
Toda F, Tanaka K, Iwata S. (1989) *J. Org. Chem.* 54, 3007-3009.
Tsyurupa M P, Davankov V A. (2002) *React. Funct. Polym.* 53, 193-203.
Urban C, McCord E F, Webster O W, Abrams L, Long H W, Gaede H, Tang P, Pines A. (1995) *Chem. Mater.* 7, 1325-1332.

van Krevelen D W. (1990) In *Properties of Polymers: Their Correlation with Chemical Structure; Their Numerical Estimation and Prediction from Additive Group Contributions*. Elsevier: Amsterdam, Netherlands.

Weber J, Su Q, Antonietti M, Thomas A. (2007) *Macromol. Rapid. Commun.* 28, 1871-1876.

Webster O W, Gentry F P, Farlee R D, Smart B E. (1992) *Makromol. Chem., Macromol. Symp.* 54(55), 477-482.

Wood C D, Tan B, Trewin A, Niu H J, Bradshaw D, Rosseinsky M J, Khimyak Y Z, Campbell N L, Kirk R, Stockel E, Cooper A I. (2007) *Chem. Mater.* 19, 2034-2048.

Yu A, Shantarovich V, Merkel T C, Bondar V I, Freeman B D, Yampolskii Y. (2002) *Macromolecules.* 35, 9513-9522.

Other advantages that are inherent to the structure are obvious to one skilled in the art. The embodiments are described herein illustratively and are not meant to limit the scope of the invention as claimed. Variations of the foregoing embodiments will be evident to a person of ordinary skill and are intended by the inventor to be encompassed by the following claims.

What is claimed is:

1. A polymer of formula (I):

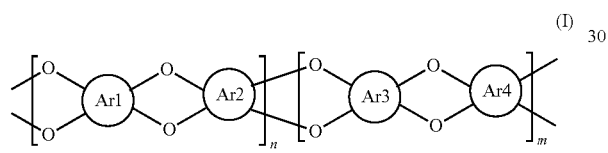

(I)

where:

n is an integer from 10 to 5,000; m is an integer from 10 to 5,000;

Ar1 and Ar3 are the same or different and are residues derived from a tetra-hydroxy aromatic monomer, the tetra-hydroxy aromatic monomer being

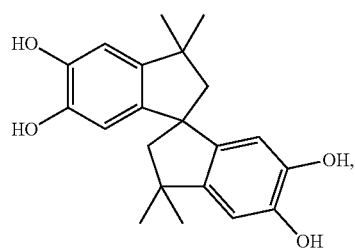

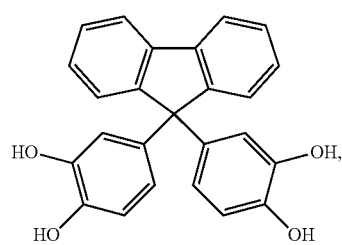

-continued

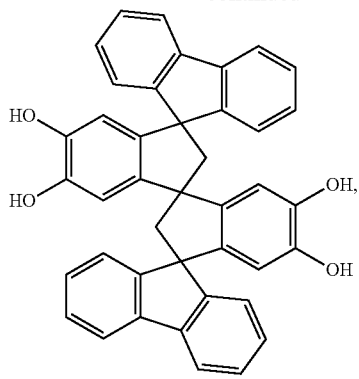

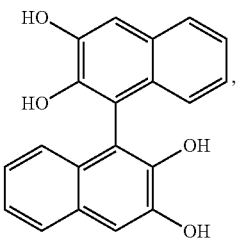

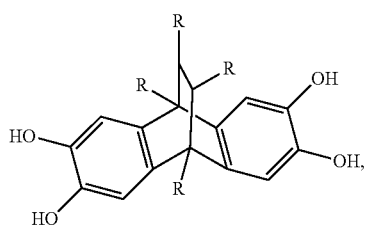

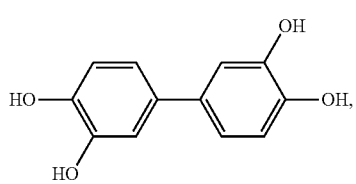

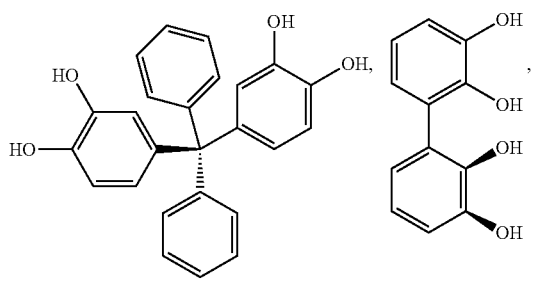

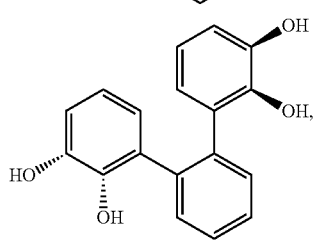

-continued

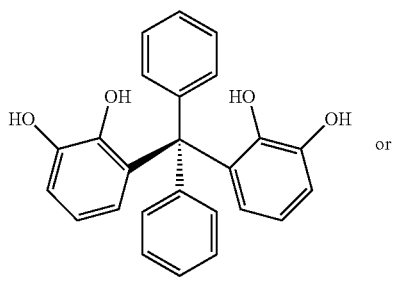
or

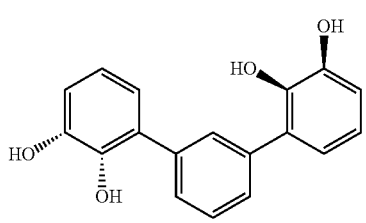

wherein R is the same or different and is H or a $C_1$-$C_8$ alkyl, $C_2$-$C_8$ alkenyl or $C_3$-$C_8$ cycloalkyl group; and, Ar2 and Ar4 are the same or different and are residues derived from a tetra-halogenated aromatic monomer, the tetra-halogenated aromatic monomer being

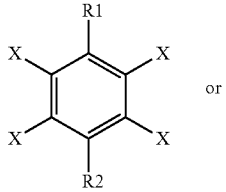
or

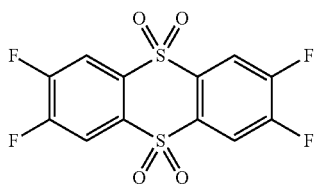

wherein X is F, Cl or Br, and R1 and R2 are the same or different and are

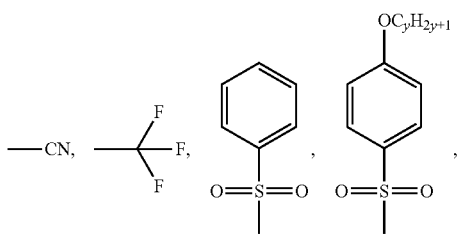

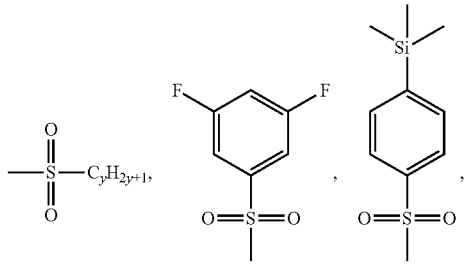

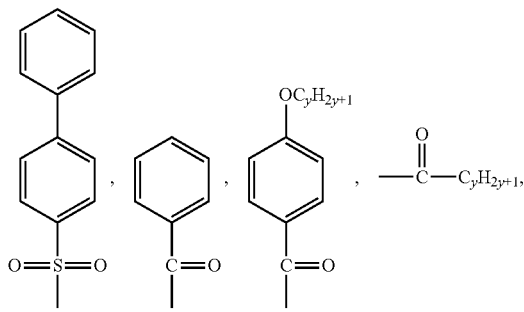

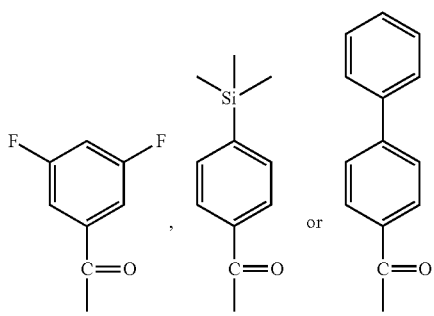

wherein y is an integer from 1 to 8;

with the proviso that when Ar1 is the same as Ar3 and Ar2 is the same as Ar4, R1 and R2 are not both —CN and when Ar1 is the same of Ar3, then Ar2 is different from Ar4 and when Ar2 is the same as Ar4, then Ar1 is different than Ar3.

2. The polymer according to claim 1, wherein n is an integer from 40 to 750 and m is an integer from 40 to 750.

3. The polymer according to claim 1, wherein Ar2 and Ar4 are the same or different and are residues derived from

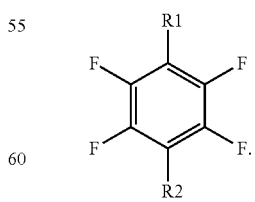

4. The polymer according to claim 3, wherein R1 and R2 are the same or different in Ar2 and are —$CF_3$, $CH_3CH_2SO_2$—, Ph-$SO_2$— or p-$CH_3O$-Ph-$SO_2$—, and wherein R1 and R2 in Ar4 are both —CN.

5. The polymer according to claim 1, wherein Ar1 and Ar3 are residues derived from

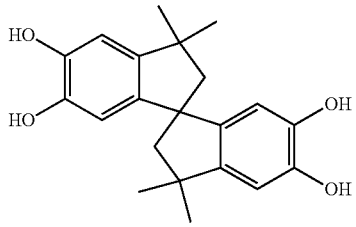 [SMILES: CC1(C)CC2(CC(C)(C)c3cc(O)c(O)cc32)c2cc(O)c(O)cc21] or

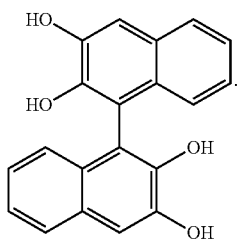

6. The polymer according to claim 1, wherein Ar1 and Ar3 are the same and are residues derived from

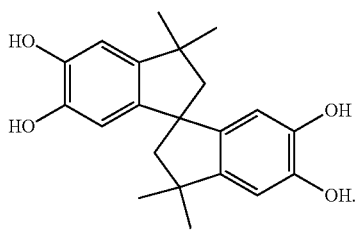

7. The polymer according to claim 1, wherein Ar1 and Ar3 are different and are residues derived from

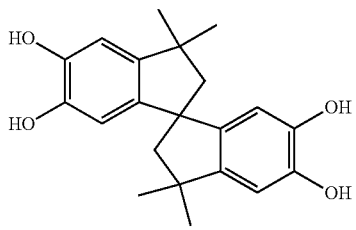 or

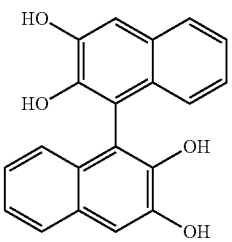

and wherein Ar2 and Ar4 are the same and are residues derived from

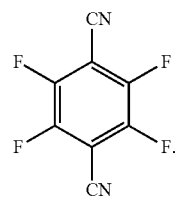

8. The polymer according to claim 1 for use as a material for gas separation, vapor separation, adsorbents or catalysis.

9. The polymer according to claim 8, wherein the material is used to separate gas mixtures of $O_2/N_2$ or $CO_2/N_2$.

10. The polymer according to claim 1 in the form of a free-standing membrane, a dense film, a coated film, a membrane on support material, a bead or a powder.

11. 2,3,7,8-tetrafluoro-5,5',10,10'-tetraoxidethianthrene.

12. A process for producing a polymer of formula (I) comprising:

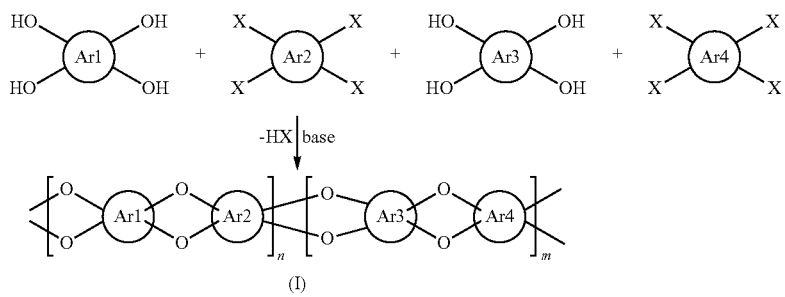

wherein Ar1, Ar2, Ar3, X, n and m are as defined in claim 1, and wherein the process is conducted in a solvent comprising an aprotic polar solvent and a non-polar solvent at a temperature in a range of 130-200° C.

13. The process according to claim 12, wherein the aprotic polar solvent comprises N, N-dimethylacetamide (DMAc).

14. The process according to claim 12, wherein the non-polar solvent comprises toluene.

15. The process according to claim 12, wherein the non-polar solvent is present in an amount 2-10 times by volume greater than the aprotic polar solvent.

16. The process according to claim 12, wherein the temperature is in a range of 155-160° C.

17. The process according to claim 12 conducted in an inert atmosphere.

18. The process according to claim 12, wherein the base comprises potassium carbonate ($K_2CO_3$).

* * * * *